(12) United States Patent
Muramatsu et al.

(10) Patent No.: US 8,828,693 B2
(45) Date of Patent: Sep. 9, 2014

(54) METHOD FOR PRODUCING ISOPROPANOL AND RECOMBINANT YEAST CAPABLE OF PRODUCING ISOPROPANOL

(75) Inventors: Masayoshi Muramatsu, Miyoshi (JP); Satoshi Yoneda, Toyota (JP)

(73) Assignee: Toyora Jidosha Kabushiki Kaisha, Aichi-ken (JP)

( * ) Notice: Subject to any disclaimer, the term of this patent is extended or adjusted under 35 U.S.C. 154(b) by 0 days.

(21) Appl. No.: 13/697,626

(22) PCT Filed: May 14, 2010

(86) PCT No.: PCT/JP2010/058190
§ 371 (c)(1),
(2), (4) Date: Nov. 13, 2012

(87) PCT Pub. No.: WO2011/142027
PCT Pub. Date: Nov. 17, 2011

(65) Prior Publication Data
US 2013/0177954 A1    Jul. 11, 2013

(51) Int. Cl.
*C12N 15/52*    (2006.01)

(52) U.S. Cl.
USPC .......................................................... 435/157

(58) Field of Classification Search
CPC .................................. C12N 15/52; C12N 9/93
USPC ............................................. 435/157, 254.2
See application file for complete search history.

(56) References Cited

U.S. PATENT DOCUMENTS

| | | |
|---|---|---|
| 6,156,532 A | 12/2000 | Kimura et al. |
| 2008/0293125 A1 | 11/2008 | Subbian et al. |
| 2010/0203604 A1 | 8/2010 | Yukawa et al. |
| 2010/0311135 A1 | 12/2010 | Takebayashi et al. |
| 2011/0165642 A1 | 7/2011 | Yukawa et al. |

FOREIGN PATENT DOCUMENTS

| | | | |
|---|---|---|---|
| EP | 2182051 A1 | 5/2010 | |
| JP | 2008-061506 A | 3/2008 | |
| JP | 2008-212044 A | 9/2008 | |
| WO | WO2009049274 | * 10/2007 | ............ C12P 21/06 |
| WO | 2007/130560 A2 | 11/2007 | |
| WO | 2007/146377 A1 | 12/2007 | |
| WO | 2008/073406 A2 | 6/2008 | |
| WO | 2009/008377 A1 | 1/2009 | |
| WO | 2009/028582 A1 | 3/2009 | |
| WO | WO2009049274 | 4/2009 | |
| WO | 2009/131040 A1 | 10/2009 | |

OTHER PUBLICATIONS

Peralta-Yahya t al., Advanced biofuel production in microbes, Biotechnol. J. 5: 147-162, published on line Jan. 18, 2010.*
Toru Jojima et al., "Production of isopropanol by metabolically engineered *Escherichia coli*", Appl. Microbiol. Biotechnol. 2008. pp. 1219-1224, vol. 77.
T. Hanai et al., "Engineered Synthetic Pathway for Isopropanol Production in *Escherichia coli*", Appl. and Environ. Microbiol., 2007, pp. 7814-7818, vol. 73, No. 24.
"Biotechnology," Edited by H.-J. Rehm et al., Second Edition, 1993, pp. 285-323, vol. 1.
Lourdes L. Bermejo et al., "Expression of Clostridium acetobutylicum ATCC 824 Genes in *Escherichia coli* for Acetone Production and Acetate Detoxification", Applied and Environmental Microbiology, Mar. 1998, pp. 1079-1085, vol. 64, No. 3.
Kenro Tokuhiro et al, "Overproduction of Geranylgeraniol by Metabolically Engineered *Saccharomyces cerevisiae*", Applied and Environmental Microbiology, Sep. 2009, pp. 5536-5543, vol. 75, No. 17.
Daniel M. Becker et al., "High-Efficiency Transformation of Yeast by Electroporation", Methods in Enzymology, 1991, pp. 182-187, vol. 194.
Albert Hinnen et al., "Transformation of yeast", Proc. Natl. Acad. Sci. USA., Apr. 1978, pp. 1929-1933, vol. 75, No. 4.
H. Ito et al., "Transformation of intact yeast cells treated with alkali cations." Journal of Bacteriology, Jan. 1983, pp. 163-168, vol. 153, No. 1.
International Search Report of PCT/JP2010/058190 dated Jun. 8, 2010.

* cited by examiner

*Primary Examiner* — Tekchand Saidha
*Assistant Examiner* — Rama P Ramanujam
(74) *Attorney, Agent, or Firm* — Sughrue Mion, PLLC

(57) ABSTRACT

Isopropanol is produced with good productivity via fermentation processes. Specifically, isopropanol is produced at a high level in a medium by culturing recombinant yeast into which an acetoacetyl CoA synthase gene and a group of genes (isopropanol synthesis-related gene group) encoding a group of enzymes for synthesis of isopropanol from acetoacetyl CoA have been introduced.

3 Claims, 1 Drawing Sheet

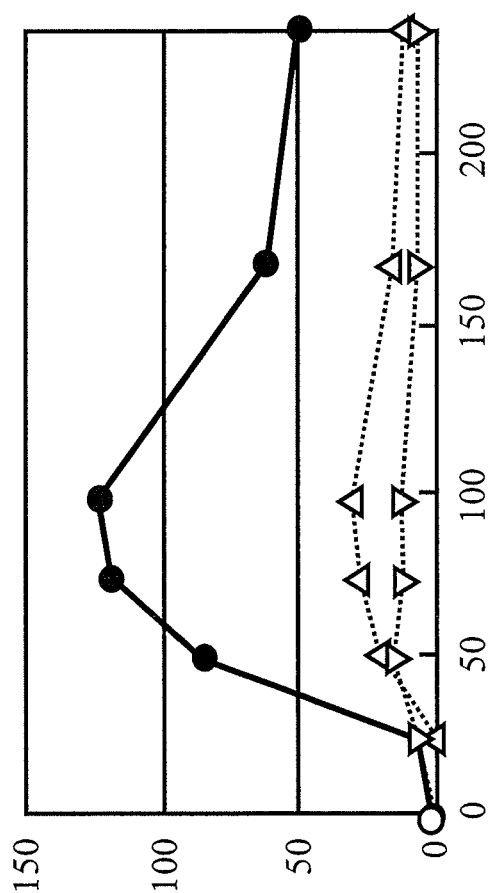

METHOD FOR PRODUCING ISOPROPANOL AND RECOMBINANT YEAST CAPABLE OF PRODUCING ISOPROPANOL

CROSS REFERENCE TO RELATED APPLICATIONS

This application is a National Stage of International Application No. PCT/JP2010/058190 filed May 14, 2010, the contents of all of which are incorporated herein by reference in their entirety.

TECHNICAL FIELD

The present invention relates to a method for producing isopropanol using recombinant yeast capable of producing isopropanol, in which an isopropanol-biosynthesis-related gene group has been incorporated, and the recombinant yeast.

BACKGROUND ART

In recent years, depletion of oil resources and global reduction of the amounts of carbon dioxide gas generated have been the subjects of dispute. Rising oil prices are predicted in the future and thus the development of alternative materials to petroleum has been required. For example, one such attempt has already been launched, involving the bioconversion of biomass, sugar, starch, fat and oil, proteins, and the like produced by plants from water and carbon dioxide gas via solar power so as to use the resultants as alternative materials to petroleum. For example, technology for producing plant-derived polylactic acid or polybutylene succinate as an alternative material to plastic produced using petroleum has been under development. Moreover, in the United States, Brazil, and the like, ethanol is produced via fermentative production from sugar, starch, or the like, blended with vehicle fuel purified from petroleum, and then used.

Furthermore, examples of chemical products that are important as resin raw-materials for industrial solvents such as paint and ink include acetone and isopropanol (which is synonymous with the term "2-propanol"). Isopropanol has been conventionally synthesized using petroleum as a raw material. However, isopropanol synthesis from biomass via fermentation processes is desired because of problems that include the depletion of petroleum and $CO_2$ reduction in air. Conventionally, it is known that *Clostridium acetobutylicum* conducts fermentative production of acetone and isopropanol together with butanol (Non-patent Document 1: Biotechnology, 2nd ed., vol. 1, pp. 285-323, 1993). It is also known that acetone is synthesized through introduction of a *Clostridium-acetobutylicum*-derived acetone synthesis gene into *Escherichia coli* (Non-patent Document 2: Appl. Environ. Microbiol., 73, 1079-1085, 1998; Patent Document 1: US2009/293125; Patent Document 2: WO 2009/008377; Patent Document 3: WO 2009/028582).

An example has been reported, whereby isopropanol is synthesized with the use of *Escherichia coli* into which an isopropanol dehydrogenase gene has been introduced in addition to a *Clostridium-acetobutylicum*-derived acetone synthesis gene (Non-patent Document 3: Appl. Environ. Microbiol., 64, 7814-7818, 2007). However, bacteria including *Escherichia coli* are problematic due to their low resistance to organic solvents. Several methods for solving this problem are known. However, the resulting resistance is insufficient for industrial production of organic solvents (Patent Document 4: WO 2007/146377; Patent Document 5: WO 2007/130560; Patent Document 6: WO 2008/073406; Patent Document 7: U.S. Pat. No. 6,156,532). Specifically, bacteria such as *Escherichia coli* are problematic due to their weak cell membranes against organic solvents. Hence, bacteria are thought to be ineffective for production of organic solvents. On the other hand, yeast is highly resistant to organic solvents, but no example of the production of an organic solvent (e.g., isopropanol or acetone) through the introduction of a gene into yeast has been reported.

PRIOR ART DOCUMENTS

Patent Documents

Patent Document 1 US 2008/293125
Patent Document 2 WO 2009/008377
Patent Document 3 WO 2009/028582
Patent Document 4 WO 2007/146377
Patent Document 5 WO 2007/130560
Patent Document 6 WO 2008/073406
Patent Document 7 U.S. Pat. No. 6,156,532

Non-Patent Documents

Non-patent Document 1 Biotechnology, 2nd Edn., vol 1, p 285-323, 1993
Non-patent Document 2 Appl. Environ. Microbiol., 73, 1079-1085, 1998
Non-patent Document 3 Appl. Environ. Microbiol., 64, 7814-7818, 2007

SUMMARY OF THE INVENTION

Object to be Achieved by the Invention

In view of the above circumstances, the objects of the present invention are to provide a method for producing isopropanol with good productivity through the use of yeast and fermentation processes, and to provide recombinant yeast having good capacity to produce isopropanol.

Means for Achieving the Object

As a result of intensive studies to achieve the above objects, the present inventors have cultured recombinant yeast into which an acetoacetyl CoA synthase gene and a gene group (isopropanol synthesis-related gene group) encoding a group of enzymes for synthesis of isopropanol from acetoacetyl CoA have been introduced. The present inventors have found that the recombinant yeast produced isopropanol at high levels, and thus completed the present invention. The present invention includes the following (1) to (19).

(1) A method for producing isopropanol, comprising culturing recombinant yeast into which an acetoacetyl CoA synthase gene and an isopropanol-biosynthesis-related gene group associated with a metabolic pathway for synthesis of isopropanol from acetoacetyl CoA are introduced and then obtaining isopropanol from the culture product.

(2) The method for producing isopropanol according to (1), wherein the acetoacetyl CoA synthase gene encodes an enzyme that catalyzes a reaction for conversion of acetyl CoA and malonyl CoA to acetoacetyl CoA.

(3) The method for producing isopropanol according to (2), wherein the acetoacetyl CoA synthase gene is a gene (ORFn gene) derived from a microorganism of the genus *Streptomyces*.

(4) The method for producing isopropanol according to (2), wherein the acetoacetyl CoA synthase gene encodes a protein having the amino acid sequence according to SEQ ID NO: 1, or a protein having an amino acid sequence that has an 80% or more identity to the amino acid sequence of SEQ ID NO: 1 and having a function of synthesizing acetoacetyl CoA from malonyl CoA and acetyl CoA.

(5) The method for producing isopropanol according to (1), wherein a gene of the isopropanol-biosynthesis-related gene group is selected from the group consisting of an acetoacetyl CoA transferase gene, an acetoacetic acid decarboxylase gene, and an isopropanol dehydrogenase gene.

(6) The method for producing isopropanol according to (1), wherein the recombinant yeast is prepared by introducing a non-endogenous gene(s) from among the acetoacetyl CoA transferase gene, the acetoacetic acid decarboxylase gene, and the isopropanol dehydrogenase gene, as a gene(s) of the isopropanol-biosynthesis-related gene group.

(7) The method for producing isopropanol according to (5) or (6), wherein the acetoacetyl CoA transferase gene comprises Clostridium-acetobutylicum-derived ctfA gene and ctfB gene.

(8) The method for producing isopropanol according to (5) or (6), wherein the acetoacetic acid decarboxylase gene is a Clostridium-acetobutylicum-derived adc gene.

(9) The method for producing isopropanol according to (5) or (6), wherein the isopropanol dehydrogenase gene is a Clostridium-beijerinckii-derived pdh gene.

(10) The method for producing isopropanol according to (1), wherein the acetoacetyl CoA synthase gene and the isopropanol-biosynthesis-related gene group are introduced into the genome of yeast as a host.

(11) Recombinant yeast, into which an acetoacetyl CoA synthase gene and an isopropanol-biosynthesis-related gene group associated with a metabolic pathway for synthesis of isopropanol from acetoacetyl CoA are introduced.

(12) The recombinant yeast according to (11), wherein the acetoacetyl CoA synthase gene encodes an enzyme that catalyzes a reaction for conversion of acetyl CoA and malonyl CoA to acetoacetyl CoA.

(13) The recombinant yeast according to (12), wherein the acetoacetyl CoA synthase gene is an acetoacetyl CoA synthase gene (ORFn gene) derived from a microorganism of the genus Streptomyces.

(14) The recombinant yeast according to (12), wherein the acetoacetyl CoA synthase gene encodes a protein having the amino acid sequence according to SEQ ID NO: 1, or a protein having an amino acid sequence that has an 80% or more identity to the amino acid sequence of SEQ ID NO: 1 and having a function of synthesizing acetoacetyl CoA from malonyl CoA and acetyl CoA.

(15) The recombinant yeast according to (11), wherein a gene of the isopropanol-biosynthesis-related gene group is selected from the group consisting of the acetoacetyl CoA transferase gene, the acetoacetic acid decarboxylase gene, and the isopropanol dehydrogenase gene.

(16) The recombinant yeast according to (11), wherein a non-endogenous gene(s) from among the acetoacetyl CoA transferase gene, the acetoacetic acid decarboxylase gene, and the isopropanol dehydrogenase gene are introduced as a gene(s) of the isopropanol-biosynthesis-related gene group.

(17) The recombinant yeast according to (15) or (16), wherein the acetoacetyl CoA transferase gene comprises Clostridium-acetobutylicum-derived ctfA gene and ctfB gene.

(18) The recombinant yeast according to (15) or (16), wherein the acetoacetic acid decarboxylase gene is a Clostridium-acetobutylicum-derived adc gene.

(19) The recombinant yeast according to (15) or (16), wherein the isopropanol dehydrogenase gene is a Clostridium-beijerinckii-derived pdh gene.

Effects of the Invention

According to the present invention, recombinant yeast highly capable of producing isopropanol can be prepared through introduction of an acetoacetyl CoA synthase gene and an isopropanol-biosynthesis-related gene group. According to the present invention, a method for producing isopropanol with good productivity can be provided through the use of recombinant yeast capable of producing isopropanol. Specifically, through the use of the method for producing isopropanol according to the present invention, productivity upon production of isopropanol to be used as fuel or a resin raw material can be improved and isopropanol production costs can be decreased.

BRIEF DESCRIPTION OF THE DRAWINGS

FIG. 1 is a characteristic diagram showing the results of measuring isopropanol production amounts for a #15-10 strain, an ERG10/#15-10 strain, and an ORFn/#15-10 strain over time.

EMBODIMENTS FOR CARRYING OUT THE INVENTION

Hereafter, the present invention is described in detail.

The method for producing isopropanol according to the present invention comprises culturing recombinant yeast into which an acetoacetyl CoA synthase gene and an isopropanol-biosynthesis-related gene group associated with a metabolic pathway for synthesis of isopropanol from acetoacetyl CoA are introduced and then obtaining isopropanol from the culture product.

Acetoacetyl CoA Synthase Gene

An acetoacetyl CoA synthase gene encodes an enzyme having activity of synthesizing acetoacetyl CoA from malonyl CoA and acetyl CoA, or activity of synthesizing acetoacetyl CoA from two molecules of acetyl CoA. In addition, an enzyme having activity of synthesizing acetoacetyl CoA from two molecules of acetyl CoA may also be referred to as thiolase.

Particularly in the present invention, an acetoacetyl CoA synthase gene encoding an enzyme that has activity of synthesizing acetoacetyl CoA from malonyl CoA and acetyl CoA is preferably used. When such an acetoacetyl CoA synthase gene encoding an enzyme that has activity of synthesizing acetoacetyl CoA from malonyl CoA and acetyl CoA is used, recombinant yeast having extremely good capacity to produce isopropanol can be prepared compared with a case in which an acetoacetyl CoA synthase gene encoding an enzyme that has activity of synthesizing acetoacetyl CoA from two molecules of acetyl CoA is used.

A gene encoding a type of acetoacetyl CoA synthase having activity of synthesizing acetoacetyl CoA from malonyl CoA and acetyl CoA has been found in actinomycetes of the genus Streptomyces, for example (JP Patent Publication (Kokai) No. 2008-61506 A). For example, a gene derived from an actinomycete of the genus Streptomyces can be used.

An example of the acetoacetyl CoA synthase gene is a gene encoding a protein having the amino acid sequence of SEQ ID NO: 1. A protein having the amino acid sequence of SEQ ID NO: 1 is acetoacetyl CoA synthase found in actinomycetes (Streptomyces sp. CL190 strain) having activity of synthesizing acetoacetyl CoA from malonyl CoA and acetyl CoA, but not having activity of synthesizing acetoacetyl CoA from two molecules of acetyl CoA (JP Patent Publication (Kokai) No. 2008-61506 A).

A gene encoding a protein having the amino acid sequence of SEQ ID NO: 1 can be obtained by a nucleic acid amplification method (e.g., PCR) using a primer pair designed in reference to JP Patent Publication (Kokai) No. 2008-61506 A and a genomic DNA obtained from the actinomycete (*Streptomyces* sp. CL190 strain) as a template.

Meanwhile, as a gene encoding a type of acetoacetyl CoA synthase (thiolase) that has activity of synthesizing acetoacetyl CoA from two molecules of acetyl CoA, a conventionally known gene; that is, an acetoacetyl CoA synthase gene of this type identified in various organisms can be used. In addition, the acetoacetyl CoA synthase gene is included in a mevalonic acid pathway existing in many biological species.

An example thereof is a *Clostridium acetobutylicum* (deposited under ATCC824)-derived thiolase gene. The *Clostridium-acetobutylicum*-derived thiolase gene is termed "th1A gene," encoding a protein having the amino acid sequence of SEQ ID NO: 2. Also, as a thiolase gene, a *Schizosaccharomyces-pombe*-, *Saccharomyces-cerevisiae*-, *Escherichia-coli*-, *Macaca-mulatta*-, *Bos-Taurus*-, *Drosophila-melanogaster*-, *Oryza-sativa*-, *Aspergillus-oryzae*-, *Bacillus-amyloliquefaciens*-, or *Clostridium-kluyveri*-derived gene can be used, for example.

In the present invention, the acetoacetyl CoA synthase gene is not limited to an actinomycete (*Streptomyces* sp. CL190 strain)-derived gene encoding a protein having the amino acid sequence of SEQ ID NO: 1. The acetoacetyl CoA synthase gene may be a gene encoding a protein that has an amino acid sequence having high similarity to the amino acid sequence of SEQ ID NO: 1 and has a function of synthesizing acetoacetyl CoA from malonyl CoA and acetyl CoA. Also, in the present invention, the acetoacetyl CoA synthase gene is not limited to a *Clostridium-acetobutylicum*-derived thiolase gene encoding a protein having the amino acid sequence of SEQ ID NO: 2. The acetoacetyl CoA synthase gene may also be a gene encoding a protein that has an amino acid sequence having high similarity to the amino acid sequence of SEQ ID NO: 2 and has a function of synthesizing acetoacetyl CoA from two molecules of acetyl CoA. Here, the term "high similarity" refers to an 80% or more identity, preferably a 90% or more identity, more preferably a 95% or more identity, and most preferably a 97% or more identity. In addition, the value of an identity is found by a program for searching for sequence similarity (may also be referred to as a homology search program). Specifically, an amino acid sequence is aligned with the amino acid sequence of SEQ ID NO: 1 or 2 and then the percentage of amino acid residues in the amino acid sequence, which have matched those in the amino acid sequence of SEQ ID NO: 1 or 2 is calculated.

Furthermore, in the present invention, the acetoacetyl CoA synthase gene may be a gene encoding a protein that has an amino acid sequence having a substitution, a deletion, an addition, or an insertion of one or a plurality of amino acids with respect to the amino acid sequence of SEQ ID NO: 1 and has a function of synthesizing acetoacetyl CoA from malonyl CoA and acetyl CoA. Also, in the present invention, the acetoacetyl CoA synthase gene may be a gene encoding a protein that has an amino acid sequence having a substitution, a deletion, an addition, or an insertion of one or a plurality of amino acids with respect to the amino acid sequence of SEQ ID NO: 2 and has a function of synthesizing acetoacetyl CoA from two molecules of acetyl CoA. Here, the term "a plurality of amino acids" refers to 2 to 30 amino acids, preferably 2 to 20 amino acids, more preferably 2 to 10 amino acids, and most preferably 2 to 5 amino acids, for example.

Moreover, in the present invention, the acetoacetyl CoA synthase gene may be a polynucleotide that hybridizes under stringent conditions to a portion of or a whole polynucleotide containing a nucleotide sequence complementary to the nucleotide sequence encoding the amino acid sequence of SEQ ID NO: 1 and encodes a protein having a function of synthesizing acetoacetyl CoA from malonyl CoA and acetyl CoA. Also, in the present invention, the acetoacetyl CoA synthase gene may be a polynucleotide that hybridizes under stringent conditions to a portion of or a whole polynucleotide containing a nucleotide sequence complementary to the nucleotide sequence encoding the amino acid sequence of SEQ ID NO: 2, and encodes a protein having a function of synthesizing acetoacetyl CoA from two molecules of acetyl CoA. Here, the expression "hybridizing under stringent conditions" means to maintain the binding under washing conditions of 60 degree C. and 2×SSC. Hybridization can be carried out by a conventionally known method such as methods described in J. Sambrook et al. Molecular Cloning, A Laboratory Manual, 2nd Ed., Cold Spring Harbor Laboratory (1989).

The above-described gene encoding acetoacetyl CoA synthase having an amino acid sequence differing from the amino acid sequence of SEQ ID NO: 1 can be isolated from actinomycetes of strains other than the *Streptomyces* sp. CL190 strain. Also, a gene encoding acetoacetyl CoA synthase having an amino acid sequence differing from the amino acid sequence of SEQ ID NO: 2 can be isolated from bacteria of the genus *Clostridium* other than *Clostridium acetobutylicum* (ATCC824), for example. Also, such genes can be obtained via modification of the polynucleotide encoding the amino acid sequence of SEQ ID NO: 1 or 2 using a method known in the art. A mutation can be introduced into a nucleotide sequence by a known technique such as a Kunkel method or a Gapped duplex method or a method according thereto. For example, a mutation is introduced using a mutagenesis kit using site-directed mutagenesis (e.g., Mutant-K or Mutant-G (both are commercial names, TAKARA)) or a LA PCR in vitro Mutagenesis Series Kit (commercial name, TAKARA).

The activity of acetoacetyl CoA synthase having an amino acid sequence differing from the amino acid sequence of SEQ ID NO: 1 can be evaluated as follows. Specifically, first, a gene encoding a protein to be evaluated is introduced into host cells so that it can be expressed and then the protein is purified by a technique such as chromatography. Malonyl CoA and acetyl CoA are added as substrates to the thus obtained buffer containing the protein to be evaluated. Subsequently, incubation is carried out at a desired temperature (e.g., 10 degree C. to 60 degree C.). After completion of the reaction, the decreased amounts of the substrates and/or the amount of the product (acetoacetyl CoA) are measured. Thus, the protein to be evaluated can be evaluated for the presence or the absence of and the degree of a function of synthesizing acetoacetyl CoA from malonyl CoA and acetyl CoA. At this time, acetyl CoA alone is added as a substrate to the thus obtained buffer containing the protein to be evaluated, and then the decreased amount of the substrate and/or the amount of the product is measured similarly. Thus, the presence or the absence of activity of synthesizing acetoacetyl CoA from two molecules of acetylCoA can be examined.

The activity of acetoacetyl CoA synthase having an amino acid sequence differing from the amino acid sequence of SEQ ID NO: 2 can be evaluated as follows. Specifically, first, a gene encoding a protein to be evaluated is introduced into host cells so that it can be expressed, and then the protein is purified by a technique such as chromatography. Acetyl CoA is added as a substrate to the thus obtained buffer containing the protein to be evaluated. Subsequently, incubation is carried out at a desired temperature (e.g., 10 degree C. to 60 degree C.), for example. After completion of the reaction, the decreased amount of the substrate and/or the amount of the product (acetoacetyl CoA) is measured. Thus, the protein to be evaluated can be evaluated for the presence or the absence of and the degree of a function of synthesizing acetoacetyl CoA from two molecules of acetyl CoA.

Isopropanol-Biosynthesis-Related Gene Group

The term "isopropanol-biosynthesis-related gene group" refers to a group that comprises a plurality of genes encoding enzymes involved in a metabolic pathway for biosynthesis of isopropanol as the final product using acetoacetyl CoA as a starting compound. Examples of enzymes involved in the metabolic pathway for isopropanol biosynthesis include acetoacetyl CoA transferase by which acetylacetic acid is synthesized using acetoacetyl CoA as a substrate, acetoacetic acid decarboxylase by which acetone is synthesized using acetylacetic acid as a substrate, and isopropanol dehydrogenase by which isopropanol is synthesized using acetone as a substrate.

Each of genes encoding these enzymes can be isolated from a microorganism capable of carrying out isopropanol biosynthesis. Examples of microorganisms capable of carrying out isopropanol biosynthesis include, but are not particularly limited to, bacteria. Examples of microorganisms capable of carrying out isopropanol biosynthesis include, but are not particularly limited to, microorganisms of the genus *Clostridium*, such as *Clostridium acetobutylicum, Clostridium beijerinckii, Clostridium saccharoperbutylacetonicum, Clostridium saccharoacetobutylicum, Clostridium aurantibutyricum, Clostridium pasteurianum, Clostridium sporogenes, Clostridium cadaveris*, and *Clostridium tetanomorphum*. Of these examples, an isopropanol-biosynthesis-related gene group derived from *Clostridium acetobutylicum* or *Clostridium beijerinckii*, the entire genome sequences of which have been analyzed, is preferably used.

In particular, as the acetoacetyl CoA transferase gene, *Clostridium-acetobutylicum*-derived ctfA gene and ctfB gene can be used. The amino acid sequence of the protein encoded by the ctfA gene is shown in SEQ ID NO: 3. The amino acid sequence of the protein encoded by the ctfB gene is shown in SEQ ID NO: 4. Also, as the acetoacetic acid decarboxylase gene, a *Clostridium-acetobutylicum*-derived adc gene can be used. The amino acid sequence of the protein encoded by the adc gene is shown in SEQ ID NO: 5. Moreover, as the isopropanol dehydrogenase gene, a *Clostridium-beijerinckii*-derived pdh gene can be used. The amino acid sequence of the protein encoded by the pdh gene is shown in SEQ ID NO: 6.

As the acetoacetyl CoA transferase (α subunit) gene other than the above ctfA gene, *Escherichia-coli*-, *Shigella-sonnei*-, *Pectobacterium-carotovorum*-, *Photorhabdus-asymbiotica*-, *Bacillus-cereus*-, *Citrobacter-koseri*-, *Streptococcus-pyogenes*-, *Clostridium-difficile*-, or *Clostridium-beijerinckii*-derived gene can be used, for example. Also, as the acetoacetyl CoA transferase (β subunit) gene other than the above ctfB gene, an *Escherichia-coli*-, *Citrobacter-koseri*-, *Haemophilus-influenzae*-, *Nitrobacter-hamburgensis*-, *Streptococcus-pyogenes*-, *Clostridium-difficile*-, or *Bacillus-weihenstephanensis*-derived gene can be used. Furthermore, as the acetoacetic acid decarboxylase gene other than the adc gene, a *Saccharopolyspora-erythraea*-, *Streptomyces-avermitilis*-, *Bradyrhizobium* sp.-, *Rhizobium-leguminosarum*-, *Burkholderia-mallei*-, *Ralstonia-solanacearum*-, *Francisella-tularensis*-, *Clostridium-botulinum*-, or *Clostridium-beijerinckii*-derived gene can be used. Furthermore, as the isopropanol dehydrogenase gene other than the pdh gene, a *Rhodococcus-rubber*-derived gene can be used.

Furthermore, the genes of the isopropanol-biosynthesis-related gene group are not limited to the above genes and may be homologous genes to *Clostridium-acetobutylicum*-derived ctfA gene, ctfB gene, adc gene, and a *Clostridium-beijerinckii*-derived pdh gene. The homologous gene can be specified by a homology search of a database storing the nucleotide sequences of genes and the amino acid sequences of proteins through the use of a known algorithm such as Blast or Fasta. The homologous genes specified using a database can be isolated from a microorganism by a known technique and then used. Specifically, a nucleic acid fragment containing the homologous gene can be obtained by a nucleic acid amplification method using genomic DNA extracted from a microorganism as a template and primers designed based on the nucleotide sequence of the thus specified homologous gene.

Furthermore, the above homologous genes derived from a microorganism of the genus *Clostridium* capable of carrying out isopropanol biosynthesis can be obtained by constructing a cDNA library of the above-described microorganism of the genus *Clostridium* capable of carrying out isopropanol biosynthesis by a known technique, and then specifying cDNA that hybridizes specifically to probes designed based on the nucleotide sequences of the *Clostridium-acetobutylicum*-derived ctfA gene, ctfB gene, and adc gene, and the *Clostridium-beijerinckii*-derived pdh gene.

In addition, a method for obtaining genes homologous to the *Clostridium-acetobutylicum*-derived ctfA gene, ctfB gene, and adc gene, and the *Clostridium beijerinckii*-derived pdh gene is not limited to the above technique. Any technique can be applied herein.

Transformation to Host Yeast

The above "acetoacetyl CoA synthase gene" and "isopropanol-biosynthesis-related gene group" are incorporated into an appropriate expression vector and then introduced into host yeast. Here, examples of the host yeast are not particularly limited, as long as it can express a gene of the present invention. Examples thereof include yeast such as *Saccharomyces cerevisiae, Schizosaccharomyces pombe*, and *Pichia pastoris.*

Furthermore, as host yeast, when the acetoacetyl CoA synthase gene having activity of synthesizing acetoacetyl CoA from malonyl CoA and acetyl CoA is used, yeast highly capable of producing fat and oil is particularly preferably used. Since malonyl CoA is one of substrates in a lipid metabolic pathway, yeast highly capable of producing fat and oil exhibits a high malonyl CoA synthesis rate and/or a high amount of malonyl CoA synthesized. Therefore, when the acetoacetyl CoA synthase gene having activity of synthesizing acetoacetyl CoA from malonyl CoA and acetyl CoA is used, improvement in isopropanol productivity can be expected with the use of yeast highly capable of producing fat and oil. Examples of such yeast highly capable of producing fat and oil include *Rhodotorula glutinis, Rhodotorula gracilis, Mortierella alpina, Lipomyces starkeyi, Trichosporon* sp., *Saccharomycopsis lipolytica, Endomyces magnusii, Cryptococcus albidus, Rhodosporidium toruloides*, and *Hansenula polymorpha.*

When yeast is used as a host, an expression vector is preferably autonomously replicable in host yeast and composed of a promoter, a ribosome binding sequence, the above gene(s), and a transcription termination sequence. Also, an expression vector may further comprise a gene for controlling promoter activity.

Furthermore, the above "acetoacetyl CoA synthase gene" and "isopropanol-biosynthesis-related gene group" are preferably introduced onto a chromosome of host yeast. Recombinant yeast in which these genes have been introduced onto such a chromosome can stably express these genes at high levels so as to be able to achieve excellent capacity to produce isopropanol. In addition, a conventionally known technique can be appropriately employed for introducing these genes onto a chromosome and examples of such a technique are not particularly limited. As an example, a method using homologous recombination with a chromosome of host yeast can be employed herein.

Furthermore, the above "acetoacetyl CoA synthase gene" and "isopropanol-biosynthesis-related gene group" are preferably introduced in multiple copies onto a chromosome of host yeast. Recombinant yeast in which these genes have been introduced in multiple copies onto a chromosome can achieve excellent capacity to produce isopropanol through high-level expression of these genes. In addition, examples of techniques for introducing these genes in multiple copies onto a chromosome are not particularly limited and conventionally known techniques therefor can be appropriately employed herein. An example thereof is a method using a vector for introduction of multiple copies.

When yeast is used as a host, *Saccharomyces cerevisiae*, *Schizosaccharomyces pombe*, or *Pichia pastoris* is used, for example. In this case, examples of a promoter are not particularly limited, as long as it can induce expression in yeast, and include a gal1 promoter, a gal10 promoter, a heat shock protein promoter, a MFα1 promoter, a PHO5 promoter, a PGK promoter, a GAP promoter, an ADH promoter, and an AOX1 promoter.

Examples of a method for introducing a recombinant vector into yeast are not particularly limited as long as it is a method for introducing DNA into yeast, and include electroporation [Becker, D. M., et al.: Methods. Enzymol., 194: 182-187 (1991)], a spheroplast method [Hinnen, A. et al.: Proc. Natl. Acad. Sci., U.S.A., 75: 1929-1933 (1978)], and a lithium acetate method [Itoh, H.: J. Bacteriol., 153: 163-168 (1983)].

Furthermore, host yeast may have at least one endogenous gene from among the above "isopropanol-biosynthesis-related genes." In this case, genes other than endogenous genes among the above "isopropanol-biosynthesis-related genes" may be introduced.

Isopropanol Production

Recombinant yeast into which the above "acetoacetyl CoA synthase gene" and "isopropanol-biosynthesis-related gene group" are introduced is cultured in medium containing a carbon source such as glucose, so that isopropanol biosynthesis proceeds. In general, if a predetermined gene is introduced into yeast for the purpose of imparting or enhancing the capacity to produce a target substance, the intended purpose cannot be achieved frequently. One of the reasons is that the stable expression of a foreign organism-derived gene in a sufficient amount is difficult. Another possible reason is that acetoacetyl CoA may not exist in cells in an amount sufficient for isopropanol biosynthesis. For example, when 2 molecules of acetyl CoA bind by thiolase activity so as to synthesize acetoacetyl CoA, the equilibrium of the reaction is in the direction of synthesis of acetyl CoA from acetoacetyl CoA. Therefore, if there is no strong reaction to convert the thus synthesized acetoacetyl CoA to the next substance, it is difficult to cause the reaction to proceed toward acetoacetyl CoA synthesis.

In addition, culture conditions for culturing yeast into which the above "acetoacetyl CoA synthase gene" and "isopropanol-biosynthesis-related gene group" are introduced are not particularly limited. Medium suitable for the auxotrophy and drug resistance of host yeast is used and yeast is cultured under general conditions.

Furthermore, the thus synthesized isopropanol is present in medium. Hence, isopropanol can be obtained from a supernatant fraction after separation of cells from the medium by means such as centrifugation. For isolation of isopropanol from a supernatant fraction, for example, an organic solvent such as ethyl acetate or methanol is added to the supernatant fraction and then sufficiently stirred. The resultant is separated into an aqueous layer and a solvent layer and then isopropanol can be extracted from the solvent layer.

EXAMPLES

Hereafter, the present invention is described in greater detail with reference to the examples, although the technical scope of the present invention is not limited to the examples.

Example 1

In the example, recombinant yeast was prepared by introducing a *Streptomyces* sp. CL190 strain-derived ORFn gene or a *Saccharomyces*-cerevisiae-derived ERG10 gene as an acetoacetyl CoA synthase gene, *Clostridium-acetobutylicum*-derived ctfA gene and ctfB gene as acetoacetyl CoA transferase gene, a *Clostridium-acetobutylicum*-derived adc gene as acetoacetic acid decarboxylase, and a *Clostridium-beijerinckii*-derived pdh gene as an isopropanol dehydrogenase gene, and then examined for its capacity to produce isopropanol.

In addition, the ORFn gene encodes acetoacetyl CoA synthase having activity of synthesizing acetoacetyl CoA from malonyl CoA and acetyl CoA. The ERG10 gene encodes acetoacetyl CoA synthase having activity of synthesizing acetoacetyl CoA from two molecules of acetyl CoA.

In the example, first, the ctfA gene, the ctfB gene and the adc gene were introduced into a chromosome using an expression vector (pEXP(Ura)-ADC-CTFA-CTFB) containing these genes, and then recombinant yeast having good capacity to produce acetone was selected. Subsequently, the pdh gene was further introduced into the chromosome of the thus selected recombinant yeast using an expression vector (pDI626PGK-T-iPDH) containing the gene, and then recombinant yeast having good capacity to produce isopropanol was selected. Next, the ORFn gene or the ERG10 gene was further introduced into the chromosome of the thus selected recombinant yeast using an expression vector (pESCpgkgap-HIS-ORFn) having the ORFn gene or an expression vector (pESCpgkgap-HIS-ERG10) having the ERG10 gene, and then the capacity to produce isopropanol was evaluated.

In addition, in the example, *Saccharomyces cerevisiae* YPH499 (Stratagene) was used as yeast. The following medium was used for culturing YPH499.

YPD Medium
2% Bacto Peptone (DIFCO)
1% Bacto Yeast extract (DIFCO)
2% D-Glucose (Wako Pure Chemical Industries, Ltd.)
SD (-URA-TRP-HIS)

SD medium produced by BIO101 was used herein. SD (-URA-TRP-HIS) medium was used after removal of uracil, tryptophan, and histidine from SD medium.

Furthermore, the genomic DNA of yeast YPH499 was prepared according to the following method. First, *Saccharomyces cerevisiae* YPH499 (Stratagene) was cultured in 3 ml of YPD medium at 30 degree C. for 1 day. The culture solution (1.5 ml) was subjected to a genomic DNA preparation kit (Gentra Puregene Yeast/Bact.kit (QIAGEN)) and thus genomic DNA was prepared.

<Preparation of pESCpgkgap-HIS-ORFn>
Preparation of pDI626PGKpro

PCR was carried out under the following conditions.
Primers (50 pmol):

```
SacI-Ppgk1 FW;
                                    (SEQ ID NO: 7)
5' TAG GGA GCT CCA AGA ATT ACT CGT GAG TAA GG 3'

SacII-Ppgk1 RV;
                                    (SEQ ID NO: 8)
5' ATA ACC GCG GTG TTT TAT ATT TGT TGT AAA AAG

TAG 3'
```

Template: genomic DNA of yeast YPH499 (0.4 µg)
Reaction solution: 50 µl of the solution containing 1× Pfu Ultra II reaction buffer (Stratagene); 10 nmol dNTP; and 1 µl of Pfu Ultra II fusion HS DNA polymerase (Stratagene)
Reaction: 95 degree C. for 5 minutes-(95 degree C. for 30 seconds, 55 degree C. for 30 seconds, and 72 degree C. for 2 minutes)×25 cycles-72 degree C. for 3 minutes-4 degree C. stock After completion of PCR, the reaction solution was purified using a MinElute PCR purification kit (QIAGEN). The thus obtained amplification fragment was digested with restriction enzymes Sac I and Sac II. Agarose gel electrophoresis was performed. A 712-bp fragment was excised and then purified using a MinElute Gel extraction kit (QIAGEN). The resultant was ligated to a pDI626GAP (APP. Env. Micro., 2009, 5536-5543) vector similarly digested with restriction enzymes Sac I and Sac II. The thus obtained sequence was subjected to sequencing, so that the preparation of the target plasmid was confirmed. The thus obtained plasmid was designated as pDI626PGKpro.

Preparation of pDI626PGK

PCR was carried out under the following conditions.
Primers (50 pmol):

```
SalI-Tpgk1 FW;
                                    (SEQ ID NO: 9)
5' TTA AGT CGA CAT TGA ATT GAA TTG AAA TCG ATA

GAT C 3'

KpnI-Tpgk1 RV2;
                                    (SEQ ID NO: 10)
5' TTA AGG TAC CGC TTC AAG CTT ACA CAA CAC 3'
```

Template: genomic DNA of yeast YPH499 (0.4 µg)
Reaction solution: 50 µl of the solution containing 1× Pfu Ultra II reaction buffer (Stratagene); and 10 nmol dNTP; 1 µl of Pfu Ultra II fusion HS DNA polymerase (Stratagene)
Reaction: 95 degree C. for 5 minutes-(95 degree C. for 30 seconds, 55 degree C. for 30 seconds, and 72 degree C. for 2 minutes)×25 cycles-72 degree C. for 3 minutes-4 degree C. stock After completion of PCR, the reaction solution was purified using a MinElute PCR purification kit (QIAGEN). The resultant was digested with restriction enzymes Sal I and Kpn I. Agarose gel electrophoresis was performed. A 330-bp fragment was excised and then purified using a MinElute Gel extraction kit (QIAGEN). The resultant was ligated to the above pDI626PGKpro vector digested with restriction enzymes Sal I and Kpn I. The thus obtained sequence was subjected to sequencing, so that the preparation of the target plasmid was confirmed. The thus obtained plasmid was designated as pDI626PGK.

Preparation of pDI626PGK-T

The above pDI626PGK was digested with restriction enzyme Sbf I. The reaction solution was purified using a MinElute PCR purification kit (QIAGEN). Subsequently, blunt-ending was performed using a TaKaRaBIO Blunting kit, and then the resultant was digested with restriction enzyme Kpn I. Agarose gel electrophoresis was performed. A 3650-bp fragment was excised and then purified using a MinElute Gel extraction kit (QIAGEN), thereby constructing a vector for ligation of the resultant. Next, pRS524GAP (APP. Env. Micro., 2009, 5536-5543) was digested with restriction enzymes PmaC I and Kpn I. Agarose gel electrophoresis was performed. A 765-bp fragment was excised and then purified using a MinElute Gel extraction kit (QIAGEN), thereby preparing an insert. These were ligated, and then joint portions of the thus obtained sequence were subjected to sequencing, so that the preparation of the target plasmid was confirmed. The thus obtained plasmid was designated as pDI626PGK-T.

Preparation of pESCgap-HIS

PCR was carried out under the following conditions.
Primers (50 pmol):

```
EcoRI-Pgap-F;
                                    (SEQ ID NO: 11)
5' CAC GGA ATT CCA GTT CGA GTT TAT CAT TAT CAA 3'

BamHI-Pgap-R;
                                    (SEQ ID NO: 12)
5' CTC TGG ATC CTT TGT TTG TTT ATG TGT GTT TAT

TC 3'
```

Template: pDI626GAP plasmid (1 ng)
Reaction solution: 50 µl of the solution containing 1× Pfu Ultra II reaction buffer (Stratagene); 10 nmol dNTP; and 1 µl of Pfu Ultra II fusion HS DNA polymerase (Stratagene)
Reaction: 95 degree C. for 2 minutes-(95 degree C. for 30 seconds, 55 degree C. for 30 seconds, and 72 degree C. for 2 minutes)×25 cycles-72 degree C. for 3 minutes-4 degree C. stock After completion of PCR, the reaction solution was purified using a MinElute PCR purification kit (QIAGEN). The resultant was digested with restriction enzymes BamH I and EcoR I. Agarose gel electrophoresis was performed. A 686-bp fragment was excised and then purified using a MinElute Gel extraction kit (QIAGEN). The resultant was ligated to a pESC-HIS (purchased from STRATAGENE) vector digested with restriction enzymes BamH I and EcoR I. The thus obtained sequence was subjected to sequencing, so that the preparation of the target plasmid was confirmed. The thus obtained plasmid was designated as pESCgap-HIS.

Preparation of pESCpgkgap-HIS
PCR was carried out under the following conditions.
Primers (50 pmol):

MunI-Ppgk1-F;
(SEQ ID NO: 13)
5' TAG GCA ATT GCA AGA ATT ACT CGT GAG TAA GG 3'

EcoRI-Ppgk1-R;
(SEQ ID NO: 14)
5' ATA AGA ATT CTG TTT TAT ATT TGT TGT AAA AAG
TAG 3'

Template: pDI626PGK plasmid (1 ng)
Reaction solution: 50 µl of the solution containing 1× Pfu Ultra II reaction buffer (Stratagene); 10 nmol dNTP; and 1 µl of Pfu Ultra II fusion HS DNA polymerase (Stratagene)
Reaction: 95 degree C. for 2 minutes-(95 degree C. for 30 seconds, 55 degree C. for 30 seconds, and 72 degree C. for 2 minutes)×25 cycles-72 degree C. for 3 minutes-4 degree C. stock After completion of PCR, the reaction solution was purified using a MinElute PCR purification kit (QIAGEN). The resultant was digested with restriction enzymes Mun I and EcoR I. Agarose gel electrophoresis was performed. A 718-bp fragment was excised and then purified using a MinElute Gel extraction kit (QIAGEN). The resultant was digested with restriction enzyme EcoR I and then ligated to the above pESCgap-HIS vector subjected to BAP treatment. Colony PCR was performed to confirm that the insert had been ligated in the correct orientation. Thus, a plasmid was prepared. The sequence was subjected to sequencing, so that the preparation of the target plasmid was confirmed. The thus obtained plasmid was designated as pESCpgkgap-HIS.

Preparation of pCR2.1-ORFn
A nucleotide sequence was designed on the basis of the nucleotide sequence of the *Streptomyces* sp. CL190 strain-derived ORFn gene, so that rare codons in *Saccharomyces cerevisiae* contained in the nucleotide sequence were replaced to high-usage codons. The thus designed nucleotide sequence is shown in SEQ ID NO: 15. Also, a nucleic acid fragment comprising the designed nucleotide sequence was synthesized in the example. Also, ggatccgccacc (SEQ ID NO: 16) was provided for an upstream untranslated region of the synthesized ORFn gene, and the synthetic DNA sequence of ctcgag was provided for a downstream untranslated region of the same. The synthetic gene was introduced into a plasmid pCR2.1 (Invitrogen). The thus obtained plasmid was designated as pCR2.1-ORFn.

Preparation of pESCpgkgap-HIS-ORFn
The above pCR2.1-ORFn was digested with restriction enzymes BamH I and Xho I, a 1002-bp fragment was excised, and then the fragment was ligated to the above pESCpgkgap-HIS vector similarly digested with restriction enzymes BamH I and Xho I. The thus obtained sequence was analyzed using restriction enzymes, so that the preparation of the target plasmid was confirmed. The thus obtained plasmid was designated as pESCpgkgap-HIS-ORFn. The pESCpgkgap-HIS-ORFn is a vector for introducing the *Streptomyces* sp. CL190 strain-derived ORFn gene (codons had been designed so that the gene can be optimally expressed in *Saccharomyces cerevisiae* YPH499) onto a chromosome of *Saccharomyces cerevisiae* YPH499. In addition, the ORFn gene was under expression control by a PGK promoter and was constantly expressed.

<Preparation of pESCpgkgap-HIS-ERG10>
PCR was carried out under the following conditions.
Primers (50 pmol):

ERG10-F;
(SEQ ID NO: 17)
5' GGG GGG ATC CGC CAC CAT GTC TCA GAA CGT TTA
CAT TGT ATC 3'

ERG10-R;
(SEQ ID NO: 18)
5' GGG GCT CGA GTC ATA TCT TTT CAA TGA CAA TAG
AGG 3'

Template: genomic DNA of YPH499 (0.3 µg)
Reaction solution: 50 µl of the solution containing 1× Pfu Ultra II reaction buffer (Stratagene); 10 nmol dNTP; and 1 µl of Pfu Ultra II fusion HS DNA polymerase (Stratagene)
Reaction: 95 degree C. for 5 minutes-(95 degree C. 30 seconds, 55 degree C. 30 seconds, 72 degree C. 2 minutes)×30 cycles-72 degree C. 3 minutes-4 degree C. stock After completion of PCR, the reaction solution was purified using a MinElute PCR purification kit (QIAGEN). The resultant was digested with restriction enzymes BamH I and Xho I. Agarose gel electrophoresis was performed. A 1209-bp fragment was excised and then purified using a MinElute Gel extraction kit (QIAGEN). The thus obtained DNA fragment was ligated to the above pESCpgkgap-HIS vector digested with restriction enzymes BamH I and Xho I. The sequence was subjected to sequencing, so that the preparation of the target plasmid was confirmed. The thus obtained plasmid was designated as pESCpgkgap-HIS-ERG10. The pESCpgkgap-HIS-ERG10 is a vector for introducing a *Saccharomyces cerevisiae* YPH499-derived thiolase gene onto a chromosome of *Saccharomyces cerevisiae* YPH499. In addition, the ORFn gene was under expression control of a PGK promoter and was constantly expressed.

<Preparation of pEXP(Ura)-ADC-CTFA-CTFB>
The *Clostridium acetobutylicum* ATCC824 strain-derived adc gene, ctfA gene, and ctfB gene were each cloned into a pT7Blue vector. After cloning of the thus obtained vector to pDI626, entry clones (pENT-ADC, pENT-CTFA, and pENT-CTFB) were prepared using a Gateway donor vector (Invitrogen). The thus obtained entry clones were incorporated into an expression vector (pDEST626 (2008)), so that pEXP (Ura)-ADC-CTFA-CTFB was prepared. This is as described in detail as follows.

Preparation of pENT-ADC
An entry clone (pENT-ADC) of the adc gene was prepared as follows.
First, PCR was carried out under the following conditions.
Primers (50 pmol):

adc-F;
(SEQ ID NO: 19)
5' ATG TTA AAG GAT GAA GTA ATT AAA CAA ATT AG 3' adc-R;
(SEQ ID NO: 20)
5' TTA CTT AAG ATA ATC ATA TAT AAC TTC AGC TC 3'

Template: genomic DNA of the above ATCC824 strain (0.4 µg)
Reaction solution: 50 µl of the solution containing 1× Pfu Ultra II reaction buffer (Stratagene); 10 nmol dNTP; and 1 µl of Pfu Ultra II fusion HS DNA polymerase (Stratagene)
Reaction: 95 degree C. for 5 minutes-(95 degree C. for 30 seconds, 60 degree C. for 30 seconds, and 72 degree C. for 2 minutes)×30 cycles-72 degree C. for 3 minutes-4 degree C. stock The 735-bp fragment amplified by PCR was cloned by blunt end cloning to a pT7Blue vector (Takara Bio Inc.) using a Perfectly Blunt Cloning Kit (Novagen). The cloned sequence was subjected to sequencing thereby confirming that it was the nucleotide sequence (CA-P0165) of the adc gene of the *Clostridium acetobutylicum* ATCC824 strain. The thus obtained plasmid was designated as pT7Blue-ADC.

Next, pT7Blue-ADC was digested with restriction enzymes BamH I and Sal I, a 771-bp fragment was excised, and then the fragment was ligated to a pDI626 vector similarly digested with restriction enzymes BamH I and Sal I. The thus obtained sequence was subjected to sequencing so that the preparation of the target plasmid was confirmed. The thus obtained plasmid was designated as pDI626-ADC.

Next, PCR was performed using the thus obtained pDI626-ADC as a template and the following primers.
Primers:

```
08-189-adc-attB1-Fw;
                                    (SEQ ID NO: 21)
5' GGG GAC AAG TTT GTA CAA AAA AGC AGG CTC

AGT TCG AGT TTA TCA TTA TC 3'

08-189-adc-attB4-Rv;
                                    (SEQ ID NO: 22)
5' GGG GAC AAC TTT GTA TAG AAA AGT TGG GTG

GGC CGC AAA TTA AAG CCT TC 3'
```

The thus obtained 1809-bp PCR product was introduced into a pDONR221 P1-P4 donor vector by gateway BP reaction. The thus obtained clone was subjected to sequencing, thereby confirming that no mutation was present in the entire nucleotide sequence of the insert. The thus obtained plasmid was designated as pENT-ADC.

Preparation of pENT-CTFA

An entry clone (pENT-CTFA) of the ctfA gene was prepared as follows.

First, PCR was carried out under the following conditions.
Primers (50 pmol):

```
ctfA-F;
                                    (SEQ ID NO: 23)
5' ATG AAC TCT AAA ATA ATT AGA TTT GAA AAT TTA

AGG 3' ctfA-R;
                                    (SEQ ID NO: 24)
5' TTA TGC AGG CTC CTT TAC TAT ATA ATT TA 3'
```

Template: genomic DNA of the above ATCC824 strain (0.4 µg)
Reaction solution: 50 µl of the solution containing 1× Pfu Ultra II reaction buffer (Stratagene); 10 nmol dNTP; and 1 µl of Pfu Ultra II fusion HS DNA polymerase (Stratagene)
Reaction: 95 degree C. for 5 minutes-(95 degree C. for 30 seconds, 60 degree C. for 30 seconds, and 72 degree C. for 2 minutes)×30 cycles-72 degree C. for 3 minutes-4 degree C. stock A 657-bp fragment amplified by PCR was similarly cloned using a Perfectly Blunt Cloning Kit (Novagen). The cloned sequence was subjected to sequencing, thereby confirming that it was the nucleotide sequence (CA-P0163) of the ctfA gene of the *Clostridium acetobutylicum* ATCC824 strain. The thus obtained plasmid was designated as pT7Blue-CTFA.

Next, pT7Blue-CTFA was digested with restriction enzymes BamH I and Sal I, a 693-bp fragment was excised, and then the fragment was ligated to a pDI626PGK vector similarly digested with restriction enzymes BamH I and Sal I. The thus obtained sequence was subjected to sequencing, so that the preparation of the target plasmid was confirmed. The thus obtained plasmid was designated as pDI626PGK-CTFA.

Next, PCR was performed using the thus obtained pDI626PGK-CTFA as a template and the following primers.
Primers:

```
08-189-ctfA-attB4r-Fw;
                                    (SEQ ID NO: 25)
5' GGG GAC AAC TTT TCT ATA CAA AGT TGG

CTT CAA GCT TAC ACA ACA CGG 3'

08-189-ctfA-attB3r-Rv;
                                    (SEQ ID NO: 26)
5' GGG GAC AAC TTT ATT ATA CAA AGT TGT

CAA GAA TTA CTC GTG AGT AAG G 3'
```

The thus obtained 1823-bp PCR product was introduced into a pDONR221 P4r-P3r donor vector by gateway BP reaction. The thus obtained clone was subjected to sequencing, thereby confirming that no mutation was present in the entire nucleotide sequence of the insert. The thus obtained plasmid was designated as pENT-CTFA.

Preparation of pENT-CTFB

An entry clone (pENT-CTFB) of the ctfB gene was prepared as follows.

First, PCR was carried out under the following conditions.
Primers (50 pmol):

```
ctfB-F;
                                    (SEQ ID NO: 27)
5' ATG ATT AAT GAT AAA AAC CTA GCG AAA G 3' ctfB-R;
                                    (SEQ ID NO: 28)
5' CTA AAC AGC CAT GGG TCT AAG TTC 3'
```

Template: genomic DNA of the above ATCC824 strain (0.4 µg)
Reaction solution: 50 µl of the solution containing 1× Pfu Ultra II reaction buffer (Stratagene); 10 nmol dNTP; and 1 µl of Pfu Ultra II fusion HS DNA polymerase (Stratagene)
Reaction: 95 degree C. for 5 minutes-(95 degree C. for 30 seconds, 60 degree C. for 30 seconds, and 72 degree C. for 2 minutes)×30 cycles-72 degree C. for 3 minutes-4 degree C. stock A 666-bp fragment amplified by PCR was cloned using a Perfectly Blunt Cloning Kit (Novagen). The cloned sequence was subjected to sequencing, thereby confirming that it was the nucleotide sequence (CA-P0164) of the ctfB gene of the *Clostridium acetobutylicum* ATCC824 strain. The thus obtained plasmid was designated as pT7Blue-CTFB.

Next, pT7Blue-CTFB was digested with restriction enzymes BamH I and Sal I, a 771-bp fragment was excised, and then the fragment was ligated to a pDI626 vector similarly digested with restriction enzymes BamH I and Sal I. The thus obtained sequence was subjected to sequencing, so that the preparation of the target plasmid was confirmed. The thus obtained plasmid was designated as pDI626-CTFB(+A).

Next, PCR was carried out under the following conditions using the following primers in order to correct mutation sites in the primers.

Primers (50 pmol):

```
BamHI-ctfB-F;
                                        (SEQ ID NO: 29)
5' TAG TGG ATC CGA TGA TTA ATG ATA AAA ACC 3' pDI626MCS-seqF;
                                        (SEQ ID NO: 30)
5' CCT AGA CTT CAG GTT GTC TAA C 3'
```

Template: pDI626-CTFB(+A)(1 ng)
Reaction solution: 50 µl of the solution containing 1× Pfu Ultra II reaction buffer (Stratagene); 10 nmol dNTP; and 1 µl of Pfu Ultra II fusion HS DNA polymerase (Stratagene)
Reaction: 95 degree C. for 2 minutes-(95 degree C. for 30 seconds, 55 degree C. for 30 seconds, and 72 degree C. for 1 minute)×20 cycles-72 degree C. for 3 minutes-4 degree C. stock After completion of PCR, the reaction solution was purified using a MinElute PCR purification kit (QIAGEN). The resultant was digested with restriction enzymes BamH I and Sal I. Agarose gel electrophoresis was performed. A 702-bp fragment was excised and then purified using a MinElute Gel extraction kit (QIAGEN). The fragment was ligated to a pDI626 vector digested with restriction enzymes BamH I and Sal I. The thus obtained sequence was subjected to sequencing, thereby confirming that mutation sites had been corrected. The thus obtained plasmid was designated as pDI626-CTFB.

Next, PCR was performed using pDI626-CTFB as a template and the following primers.
Primers:

```
08-189-ctfB-attB3-Fw;
                                        (SEQ ID NO: 31)
5' GGG GAC AAC TTT GTA TAA TAA AGT TGG

GCC GCA AAT TAA AGC CTT C 3'

08-189-ctfB-attB2-Rv;
                                        (SEQ ID NO: 32)
5' GGG GAC CAC TTT GTA CAA GAA AGC TGG

GTA CAG TTC GAG TTT ATC ATT ATC 3'
```

The thus obtained 1737-bp PCR product was introduced into a pDONR221 P3-P2 donor vector by gateway BP reaction. The thus obtained clone was subjected to sequencing, thereby confirming that no mutation site was present in the entire nucleotide sequence of the insert. The thus obtained plasmid was designated as pENT-CTFB.
Preparation of pDEST626 (2008)
PCR was carried out under the following conditions.
Primers:

```
SacI-convA-F;
                                        (SEQ ID NO: 33)
5' TAG GGA GCT CAT CAC AAG TTT GTA CAA AAA AGC

TG 3'

KpnI-convA-R;
                                        (SEQ ID NO: 34)
5' TTA AGG TAC CAT CAC CAC TTT GTA CAA GAA AGC 3'
```

Template: RfA (Invitrogen, Gateway Vector Conversion System) (0.5 ng)
Primers (50 pmol):
Reaction solution: 50 µl of the solution containing 1× Pfu Ultra II reaction buffer (Stratagene); 10 nmol dNTP; and 1 µl of Pfu Ultra II fusion HS DNA polymerase (Stratagene)
Reaction: 95 degree C. for 2 minutes-(95 degree C. for 30 seconds, 55 degree C. for 30 seconds, and 72 degree C. for 1 minute and 30 seconds)×20 cycles-72 degree C. for 3 minutes-4 degree C. stock In addition, RfA used as a template was Reading Frame Cassette A of a Gateway Vector Conversion System. After completion of PCR, the reaction solution was purified using a MinElute PCR purification kit (QIAGEN). The resultant was digested with restriction enzymes Sac I and Kpn I. Agarose gel electrophoresis was performed. A 1717-bp fragment was excised and then purified using a MinElute Gel extraction kit (QIAGEN). The fragment was ligated to a pDI626GAP vector (APP. Env. Micro., 2009, 5536) digested with restriction enzymes Sac I and Kpn I. The thus obtained sequence was subjected to sequencing, so that the preparation of the target plasmid was confirmed. The thus obtained plasmid was designated as pDEST626 (2008).
Preparation of pEXP(Ura)-ADC-CTFA-CTFB The above-obtained 3 entry clones (pENT-ADC, pENT-CTFA, and pENT-CTFB) were incorporated into the expression vector pDEST626 (2008) by Gateway LR reaction. The thus obtained clone was confirmed for insert size by PCR, thereby confirming that recombination had been performed correctly. Sequencing was performed to confirm that no error was found in the sequence. The thus obtained plasmid was designated as pEXP(Ura)-ADC-CTFA-CTFB.
<Preparation of pDI626PGK-T-iPDH>
Preparation of pCR2.1-iPDH A nucleotide sequence was designed on the basis of the nucleotide sequence of the *Clostridium beijerinckii* NRRL B593-derived pdh gene (registered in GenBank), so that the frequencies of rare codons (*Saccharomyces cerevisiae*) contained in the nucleotide sequence were increased. Also, a nucleic acid fragment comprising the designed nucleotide sequence was synthesized in the example (SEQ ID NO: 35). Also, GGGGTTTCCGCGGTCTAGAGCCACC (SEQ ID NO: 36) was provided for an upstream untranslated region of the synthesized pdh gene, and the synthetic DNA sequence of GGATCCGTCGACGGGG (SEQ ID NO: 37) was provided for a downstream untranslated region of the same. The plasmid was designated as pCR2.1-iPDH.
Preparation of pDI626PGK-T-iPDH Next, pCR2.1-iPDH was digested with restriction enzymes Sac II and Sal I, a 1080-bp fragment was excised, and then the fragment was ligated to the above pDI626PGK-T vector similarly digested with restriction enzymes Sac II and Sal I. The thus obtained sequence was subjected to sequencing, so that the preparation of the target plasmid was confirmed. The thus obtained plasmid was designated as pDI626PGK-T-iPDH. pDI626PGK-T-iPDH is a vector for introducing the *Clostridium beijerinckii* NRRL B593 strain-derived pdh gene (codons had been designed so that the gene can be optimally expressed in *Saccharomyces cerevisiae* YPH499) onto a chromosome of *Saccharomyces cerevisiae* YPH499. In addition, the pdh gene was under expression control by a PGK promoter and was constantly expressed.
<Transformation 1>

In the example, first, the above-constructed pEXP(Ura)-ADC-CTFA-CTFB was linearized via cleavage with restriction enzymes Aat II and BssH II. After ethanol precipitation, the resultant was dissolved in 0.1×TE Buffer, and then *Saccharomyces cerevisiae* YPH499 (Stratagene) was transformed using a Frozen EZ yeast transformation kit (Zymoresearch). The thus obtained clones were subjected to colony PCR, and thus the introduction of the adc gene, the ctfA gene, and the ctfB gene was confirmed in 25 clones. Also, the acetone production amounts of the thus obtained clones were measured and the clone with the highest acetone production amount was designated as #3-17.

<Transformation 2>

In the example, next, the above-constructed pDI626PGK-T-iPDH was linearized via cleavage with restriction enzymes Aat II and BssH II. After ethanol precipitation, the resultant was dissolved in 0.1×TE Buffer, and then the yeast #3-17 producing acetone at the highest level was transformed using a Frozen EZ yeast transformation kit (Zymoresearch). The thus obtained 14 clones were subjected to colony PCR, thereby confirming that the pdh gene had been introduced in 13 clones. The isopropanol production amounts of the thus obtained clones were measured and a clone with the highest isopropanol production amount was designated as #15-10.

<Transformation 3>

In the example, next, #15-10 was transformed using the above-constructed pESCpgkgap-HIS-ERG10 (0.5 μg). Transformation was performed according to the method of a Frozen EZ yeast transformation kit (Zymoresearch) in a manner similar to the above. After transformation, the resultant was applied to SD(-URA-TRP-HIS) medium and then cultured for 5 days at 30 degree C. Colonies that had appeared were subcultured. After confirmation of the introduction of the ERG10 gene by PCR, the thus obtained strain was designated as an ERG10/#15-10 strain.

Also, similarly, #15-10 was transformed using the above-constructed pESCpgkgap-HIS-ORFn (0.5 μg). After confirmation of the introduction of the ORFn gene by PCR, the thus obtained strain was designated as an ORFn/#15-10 strain.

<Isopropanol Productivity Test>

The isopropanol productivity of the recombinant yeast strains (the ERG10/#15-10 strain and the ORFn/#15-10 strain) prepared in Transformation 3 above was evaluated. Specifically, first, 30 μl of a recombinant yeast solution thawed from each glycerol stock was inoculated in a disposable test tube (made of glass, 16×100 mm, ASAHI TECHNO GLASS) containing 3 ml of medium. The test tube was shaken at 30 degree C. and 130 strokes/min (Takasaki two-stage shaking incubator TXY-16R-2FL-type) for 66 hours, so that a pre-culture solution was prepared. Next, 1 ml of the pre-culture solution was inoculated into a 300-ml Erlenmeyer flask containing 100 ml of medium, and then rotation culture was performed with a two-stage incubator (IFM-II—S-type, Oriental Giken Inc.) at 30 degree C. and 130 rpm for 240 hours. O. D. was measured at 600 nm and sampling was performed at 24H, 48H, 72H, 96H, 168H, and 240H after the initiation of the culture.

A culture solution (3 ml) was added to a screw capped test tube (TST SCR 16-100; 16×100 mm, ASAHI TECHNO GLASS) and then centrifuged at room temperature and 1000 g for 5 minutes (TOMY LC-230-type). A supernatant (2 ml) was added to a HSS vial with a capacity of 20 ml. After sealing of the vial, heat treatment was performed at 60 degree C. for 15 minutes. Thereafter, acetone and isopropanol were analyzed by HSS-GC/MS analysis. A standard solution with a known concentration was prepared in advance to draw a calibration curve, and thus the concentrations of the samples were quantitatively determined. HSS-GC/MS analytical conditions are as shown below.

Head Space Sampler Analytical Conditions
  Head space sampler: HP7694 (Hewlett-Packard)
  Zone Temp.
  Oven; 60 degree C.
  Loop; 150 degree C.
  TR.LINE; 200 degree C.
  Event Time:
  GC CYCLE TIME; 35 min
  Vial EQ TIME; 15 min
  PRESSURIZ. TIME; 0.50 min
  Loop Fill TIME; 0.2 min
  Loop EQ TIME; 0.2 min
  INJECT TIME; 1.00 min
  Vial Parameter
  SHAKE; HIGH
  Others
  Vial pressurization; 15 psi
  Loop size; 3 ml GC-MS Analytical Conditions
GC/MS: HP6890/5973 GC/MS system (Hewlett-Packard)
Column: J&W DB-624 (0.32 mm×60 m, film thickness: 1.8 μm)
Inlet temperature: 260 degree C.
Detector temperature: 260 degree C.
Injection parameter:
  Split ratio; 1/20
  Carrier gas; helium 1.0 ml/minute
  Oven (heating conditions); 40 degree C. for 5 minutes→heat (5 degree C./minute) to 75 degree C.→heat (100 degree C./minute) to 260 degree C.->260 degree C. for 16 minutes <Measurement Results>

FIG. 1 shows the results of measuring over time the isopropanol production amounts of the #15-10 strain prepared in Transformation 2 above, and the ERG10/#15-10 strain and the ORFn/#15-10 strain prepared in Transformation 3 above. In FIG. 1, downward-pointing triangles denote the #15-10 strain, upward-pointing triangles denote the ERG10/#15-10 strain, and black circles denote the ORFn/#15-10 strain. Also, after the initiation of the culture, isopropanol production amounts at hour 96 were compared and the results are shown in Table 1.

TABLE 1

| Strain | Production (mg/L) |
|---|---|
| YPH499 | 0.0 |
| # 15-10 strain | 14.3 |
| ERG/# 15-10 strain | 29.8 |
| ORFn/# 15-10 strain | 122.6 |

Time for culture (h): 96 hours

As understood from FIG. 1 and Table 1, it was revealed that isopropanol productivity can be significantly improved with the use of the recombinant yeast in which the acetoacetyl CoA synthase gene had been introduced in addition to the isopropanol-biosynthesis-related gene group associated with the metabolic pathway for synthesis of isopropanol from acetoacetyl CoA. In particular, isopropanol productivity was drastically improved in the case of introduction of the acetoacetyl CoA synthase gene encoding the enzyme having activity of synthesizing acetoacetyl CoA from malonyl CoA and acetyl CoA, compared with the case of introduction of the acetoacetyl CoA synthase gene (thiolase) encoding the enzyme having activity of synthesizing acetoacetyl CoA from two molecules of acetyl CoA. It was considered that since yeast used as a host herein naturally had capacity of lipid synthesis, the yeast naturally had malonyl CoA in an amount sufficient for use in the lipid synthesis pathway. Therefore, the results revealed that through introduction of the acetoacetyl CoA synthase gene encoding the enzyme having activity of synthesizing acetoacetyl CoA from malonyl CoA and acetyl CoA and the isopropanol-biosynthesis-related gene group associated with the metabolic pathway for synthesis of isopropanol from acetoacetyl CoA into particularly yeast having good capacity of lipid synthesis, recombinant yeast having excellent isopropanol productivity can be prepared.

Reference Example 1

In this reference example, *Escherichia coli* was used as a host. Specifically, an acetoacetyl CoA synthase gene was further introduced into recombinant *Escherichia coli* in which an isopropanol-biosynthesis-related gene group associated with a metabolic pathway for synthesis of isopropanol from acetoacetyl CoA had been introduced, so as to prepare the recombinant *Escherichia coli*, and then isopropanol productivity was evaluated.
<Preparation of Genomic DNA of *Clostridium acetobutylicum*>

The *Clostridium acetobutylicum* ATCC (824) strain was anaerobically cultured according to a conventional method in 3 ml of reinforced *Clostridium* medium (Difco) at 30 degree C. for 2 days. Genomic DNA was prepared from 1.5 ml of the culture solution using a genomic DNA preparation kit (Gentra Puregene Yeast/Bact.kit (QIAGEN)).
<Preparation of pT7Blue-CAC2873>

A thiA gene that is a *Clostridium-acetobutylicum*-derived thiolase gene was cloned as follows. First, PCR was performed using the following primers.

```
CAC2873-F:
                                        (SEQ ID NO: 38)
5'-ATG AAA GAA GTT GTA ATA GCT AGT GCA G-3'

CAC2873-R:
                                        (SEQ ID NO: 39)
5'-CTA GCA CTT TTC TAG CAA TAT TGC TG-3'
```

In PCR, 0.1 µg of the genomic DNA of the above-prepared *Clostridium acetobutylicum* ATCC (824) strain was used as a template. Also, the above primer pair was used at a concentration of 50 pmol. The composition of the reaction solution is as follows. Fifty (50) µl of the solution contained 10 nmol of dNTP and 1 µl of Pfu Ultra II fusion HS DNA polymerase (Stratagene) in 1× Pfu Ultra II reaction buffer (Stratagene). PCR thermal cycles are as follows. After treatment at 95 degree C. for 5 minutes, a cycle of 95 degree C. for 30 seconds, 60 degree C. for 30 seconds, and 72 degree C. for 3 minutes was repeated 30 times, followed by treatment at 72 degree C. for 3 minutes. After completion of the reaction, the resultant was stored at 4 degree C.

An about 1.2-kb fragment amplified by PCR was cloned by blunt end cloning to a pT7-Blue vector using a Perfectly Blunt Cloning Kit (Novagen). The cloned sequence was subjected to sequencing thereby confirming that it was the thiA gene of the *Clostridium acetobutylicum* ATCC (824) strain. The thus obtained plasmid was designated as pT7Blue-CAC2873.
<Preparation of pCDFDuet-thiA>

An expression vector for expression of the above thiA gene in *Escherichia coli* was constructed as follows. First, PCR was performed using the following primers.

```
acat-NdeI-F:
                                        (SEQ ID NO: 40)
5'-AAA CAT ATG AAA GAA GTT GTA ATA GC-3' acat-XhoI-R:
                                        (SEQ ID NO: 41)
5'-AAA CTC GAG CTA GCA CTT TTC TAG CAA T-3'
```

In PCR, the above-prepared pT7Blue-CAC2873 was used as a template. Also, the above primer pair was used at a concentration of 10 pmol. The composition of the reaction solution is as follows. Fifty (50) µl of the solution contained 12.5 nmol dNTP and 1 µl of Pfu Ultra™ II fusion HS DNA polymerase (Stratagene) in 1× Pfu Ultra™ II reaction buffer (Stratagene). PCR thermal cycles are as follows. After treatment at 95 degree C. for 2 minutes, a cycle of 95 degree C. for 20 seconds, 43 degree C. for 20 seconds, and 72 degree C. for 40 seconds was repeated 5 times, and then a cycle of 95 degree C. for 20 seconds, 50 degree C. for 20 seconds, and 72 degree C. for 40 seconds was repeated 30 times, followed by treatment at 72 degree C. for 3 minutes. After completion of the reaction, the resultant was stored at 4 degree C.

An about 1.2-bp DNA fragment amplified by PCR was purified using a MinElute PCR Purification Kit and then cloned to a, pCR-Blunt II-Topo vector using a Zero Blunt TOPO PCR Cloning Kit. The thus obtained vector was designated as pCR-Blunt II-TOPO-thiA. pCR-Blunt II-TOPO-thiA was cleaved with Nde I and Xho I, an about 1.2-Kbp DNA fragment was purified by agarose gel electrophoresis, and then the fragment was inserted to the Nde I-Xho I site of pCDF-Duet (Novagen). The thus obtained plasmid was designated as pCDFDuet-thiA.
<Preparation of pCDFDuet-orfN>

A *Clostridium-acetobutylicum*-derived acetoacetyl CoA synthase gene for synthesis of acetoacetyl CoA from malonyl CoA and acetyl CoA was cloned as described below. First, PCR was performed using the following primers.

```
OrfN-NdeI-F:
                                        (SEQ ID NO: 42)
5'-AAA CAT ATG ACC GAC GTC CGA TTC CGC AT 3'

OrfN-XhoI-R:
                                        (SEQ ID NO: 43)
5'-AAA CTC GAG TTA CCA CTC GAT CAG GGC GA 3'
```

In PCR, 20 ng of pHISORFn was used as a template. As pHISORFn, the one described in JP Patent Publication (Kokai) No. 2008-61506 A was used. Also, the above primer pair was used at a concentration of 15 pmol. The composition of the reaction solution is as follows. Fifty (50) µl of the solution contained 10 nmol of dNTP and 0.5 µl of PrimeSTAR HS DNA Polymerase (Takara Bio Inc.) in 1× PrimeSTAR GC Buffer (Mg$^{2+}$ plus) (Takara Bio Inc.). PCR thermal cycles are as follows. After treatment at 94 degree C. for 1 minute, a cycle of 98 degree C. for 10 seconds, 53 degree C. for 5 seconds, and 72 degree C. for 1 minute was repeated 5 times, and then a cycle of 98 degree C. for 10 seconds, 60 degree C. for 5 seconds, and 72 degree C. for 1 minute was repeated 30 times, followed by treatment at 72 degree C. for 5 minutes. After completion of the reaction, the resultant was stored at 4 degree C.

An about 1-Kbp DNA fragment amplified by PCR was purified using a MinElute PCR Purification Kit and then cloned to a pCR-Blunt II-Topo vector using a Zero Blunt TOPO PCR Cloning Kit. The thus obtained vector was designated as pCR-Blunt II-TOPO-orfN. pCR-Blunt II-TOPO-orfN was cleaved with Nde I and Xho I, an about 1-Kbp DNA fragment was purified by agarose gel electrophoresis, and then the fragment was inserted to the Nde I-Xho I site of pCDF-Duet (Novagen). The thus obtained plasmid was designated as pCDFDuet-orfN.
<Construction of pETDuet-ctfAB>

A ctfA gene and a ctfB gene that are *Clostridium-acetobutylicum*-derived acetoacetyl CoA transferase genes were cloned. First, PCR was performed using genomic DNA prepared as described above as a template. In PCR, Pfu Ultra II fusion HS DNA polymerase (STRATAGEN) and the following primers (underlined portions are restriction enzyme sites) were used.

```
ctfAB-NdeI-F:
                                          (SEQ ID NO: 44)
5'-ATT CAT ATG AAC TCT AAA ATA ATT AGA TTT GAA

AAT TTA AGG TC-3' ctfAB-NdeI-R:
                                          (SEQ ID NO: 45)
5'-AGA CTC GAG CTA AAC AGC CAT GGG TCT AAG-3'
```

The composition of the PCR solution is as follows.

TABLE 2

| Reaction composition: total reaction volume | 50 μl |
|---|---|
| Clostridium genome DNA (0.4 μg/μl) | 1 μl (final 0.4 μg) |
| PfuUltra II fusion HS DNA polymerase | 1 μl |
| 10 x PfuUltra II reaction Buffer | 5 μl |
| dNTP Mix (2.5 mM each dNTP) | 5 μl (final 0.25 mM each dNTP) |
| ctfAB-NdeI-F (10 μM) | 1 μl |
| ctfAB-NdeI-R (10 μM) | 1 μl |
| Sterile water | 36 μl |

PCR thermal cycles are as follows. After treatment at 95 degree C. for 2 minutes, a cycle of 95 degree C. for 30 seconds, 54.8 degree C. for 30 seconds, and 72 degree C. for 2 minutes was repeated 30 times, followed by treatment at 72 degree C. for 7 minutes. After completion of the reaction, the resultant was stored at 4 degree C.

PCR (Eppendruf) was performed under the following conditions. A 1324-bp fragment was excised by 0.8% agarose gel electrophoresis. The excised fragment was purified using a QIAquick Gel Extraction Kit (QIAGEN) and then digested with Nde I and Xho I. After further purification with a QIAquick PCR Purification Kit (QIAGEN), the resultant was inserted to the Nde I, Xho I site of pETDuet-1 (Merck & Co., Inc.). The thus obtained sequence was subjected to sequencing, so that the preparation of the target plasmid was confirmed. The thus obtained plasmid was designated as pETDuet-ctfAB.

<Construction of pETDuet-ADC>

An adc gene that is a *Clostridium-acetobutylicum*-derived acetoacetic acid decarboxylase gene was cloned. First, PCR was performed using the genomic DNA prepared above as a template. In PCR, Pfu Ultra II fusion HS DNA polymerase (STRATAGEN) and the following primers (underlined portions are restriction enzyme sites) were used.

```
adc-SalI-F:
                                          (SEQ ID NO: 46)
5'-CAC GTC GAC AAG GAG ATA TAA TGT TAA AGG ATG

AAG TAA TTA AAC A-3' adc-NotI-R:
                                          (SEQ ID NO: 47)
5'-CAC GCG GCC GCT TAC TTA AGA TAA TCA TAT ATA

ACT TCA GC-3'
```

The composition of the PCR solution is as follows.

TABLE 3

| Reaction composition: total reaction volume | 100 μl |
|---|---|
| Clostridium genome DNA (0.4 μg/μl) | 2 μl (final 0.8 μg) |
| PfuUltra II fusion HS DNA polymerase | 2 μl |
| 10 x PfuUltra II reaction Buffer | 10 μl |
| dNTP Mix (2.5 mM each dNTP) | 10 μl (final 0.25 mM each dNTP) |
| adc-SalI-F (10 μM) | 2 μl |
| adc-NotI-R (10 μM) | 2 μl |
| Sterile water | 62 μl |

PCR thermal cycles are as follows. After treatment at 95 degree C. for 2 minutes, a cycle of 95 degree C. for 20 seconds, 54.8 degree C. for 20 seconds, and 72 degree C. for 3 minutes was repeated 30 times, followed by treatment at 72 degree C. for 3 minutes. After completion of the reaction, the resultant was stored at 13 degree C.

PCR (Eppendruf) was performed under the above conditions, and thus a 735-bp fragment was excised by 1% agarose gel electrophoresis. The fragment excised using a QIAquick Gel Extraction Kit (QIAGEN) was purified and then digested with Sal I and Not I. Furthermore, after purification using a QIAquick PCR Purification Kit (QIAGEN), the resultant was inserted to the Sal I, Not I site of pETDuet-1 (Merck & Co., Inc.). The thus obtained sequence was subjected to sequencing, so that the preparation of the target plasmid was confirmed. The thus obtained plasmid was designated as pETDuet-ADC.

<Construction of pETDuet-ADC-ctfAB>

An expression vector for expression of the above ctfA gene, ctfB gene, and adc gene in *Escherichia coli* was constructed as follows. First, the above-prepared pETDuet-ADC was digested with Sal I and Not I, a 753-bp fragment containing the adc gene was excised by 0.8% agarose gel electrophoresis, and then the fragment was purified using a QIAquick Gel Extraction Kit (QIAGEN). Also, the above-prepared pETDuet-ctfAB was digested with Sal I and Not I, and then the thus obtained 6677-bp fragment was ligated to the above fragment. The thus obtained vector was designated as pETDuet-ADC-ctfAB.

<Construction of pCOLADuet-PDH>

A pdh gene that is a *Clostridium-beijerinckii*-derived isopropanol dehydrogenase gene was cloned. First, PCR was performed using the pCR2.1-iPDH prepared in Example 1 above as a template as follows. In PCR, Pfu Ultra II fusion HS DNA polymerase (STRATAGEN) and the following primers (underlined portions are restriction enzyme sites) were used.

```
PDH-EcoRI-F:
                                          (SEQ ID NO: 48)
5'-GGA ATT CCA TGA AAG GTT TCG CAA TGT T-3'

PDH-PstI-R:
                                          (SEQ ID NO: 49)
5'-AAC TGC AGA ACC AAT GCA TTG GTT ACA AAA TGA

CTA CGG-3'
```

The composition of the PCR solution is as follows.

TABLE 4

| Reaction composition: total reaction volume | 50 μl |
|---|---|
| pCR2.1-iPDH (0.36 μg/μl) | 1 μl (final 0.36 μg) |
| PfuUltra II fusion HS DNA polymerase | 1 μl |

TABLE 4-continued

| | |
|---|---|
| 10 × PfuUltra II reaction Buffer | 5 µl |
| dNTP Mix (2.5 mM each dNTP) | 5 µl (final 0.25 mM each dNTP) |
| PDH-EcoRI-F (10 µM) | 1 µl |
| PDH-PstI-R (10 µM) | 1 µl |
| Sterile water | 36 µl |

PCR thermal cycles are as follows. After treatment at 95 degree C. for 2 minutes, a cycle of 95 degree C. for 30 seconds, 50 degree C. for 30 seconds, and 72 degree C. for 2 minutes was repeated 30 times, followed by treatment at 72 degree C. for 7 minutes. After completion of the reaction, the resultant was stored at 4 degree C.

PCR (Eppendruf) was performed under the following conditions, a 1056-bp fragment was excised by 0.8% agarose gel electrophoresis. The fragment was purified using a MiniElute Gel Extraction Kit (QIAGEN) and then digested with EcoR I and Pst I. After purification with a QIAquick PCR Purification Kit (QIAGEN), the resultant was inserted to the EcoR I, Pst I site of pCOLADuet-1 (Merck & Co., Inc.). The thus obtained sequence was subjected to sequencing, so that the preparation of the target plasmid was confirmed. The thus obtained plasmid was designated as pCOLADuet-PDH.

<Preparation of Recombinant *Escherichia coli*>

*Escherichia coli* NovaBlue (DE3) classified as an *Escherichia coli* BL21 (DE3) *Escherichia coli* K strain (Takara Bio Inc.) was transformed with combinations A to F of the above-prepared pCDFDuet-thiA, pCDFDuet-orfN, pETDuet-ADC-ctfAB, and pCOLADuet-PDH shown in Table below. Recombinant *Escherichia coli* strains resulting from transformation of *Escherichia coli* BL21 (DE3) with the expression vector combinations A to F were designated as A/BL21, B/BL21, C/BL21, D/BL21, E/BL21, and F/BL21, respectively. Recombinant *Escherichia coli* strains resulting from transformation of *Escherichia coli* NovaBlue (DE3) with the expression vector combinations A to F were designated as A/NB, B/NB, C/NB, D/NB, E/NB, and F/NB, respectively.

TABLE 5

| | A | B | C | D | E | F |
|---|---|---|---|---|---|---|
| pCDFDuet-thiA | | | + | | + | |
| pCDFDuet-orfN | | | | + | | + |
| pETDuet-ADC-ctfAB | + | + | + | + | + | + |
| pCOLADuet-PDH | | + | | | + | + |

First, a trace element with the following composition was prepared upon culture of the thus obtained recombinant *Escherichia coli*.

TABLE 6

| Reagent | 5M HCl (final concentration) |
|---|---|
| FeSO$_4$·7H$_2$O | 40.0 g |
| MnSO$_4$·H$_2$O | 10.0 g |
| Al$_2$(SO$_4$)$_3$ | 28.3 g |
| CoCl$_2$·6H$_2$O | 4.0 g |
| ZnSO$_4$·7H$_2$O | 2.0 g |
| Na$_2$MoO$_4$·2H$_2$O | 2.0 g |
| CuCl$_2$·2H$_2$O | 1.0 g |
| H$_3$BO$_4$ | 0.5 g |

Furthermore, SD-7 medium was prepared as follows. NH$_4$Cl (7.0 g), KH$_2$PO$_4$ (1.5 g), Na$_2$HPO$_4$ (1.5 g), K$_2$SO$_4$ (0.35 g), MgSO$_4$·7H$_2$O (0.17 g), yeast extract (5.0 g, Difco), and a trace element (0.8 ml) were dissolved in 0.8 L of deionized water, and then the solution was adjusted with 5M NH$_4$OH to pH 7.0. The total volume of the solution was adjusted with deionized water to 1 L and then the solution was autoclave-sterilized.

Furthermore, SD-8 medium was prepared as follows. NH$_4$Cl (7.0 g), KH$_2$PO$_4$ (7.5 g), Na$_2$HPO$_4$ (7.5 g), K$_2$SO$_4$ (0.85 g), MgSO$_4$·7H$_2$O (0.17 g), a yeast extract (10.0 g, Difco), and a trace element (0.8 ml) were dissolved in 1 L of deionized water and then the mixture was autoclave-sterilized.

Furthermore, when each recombinant *Escherichia coli* strain above was cultured in the SD-7 medium or the SD-8 medium, antibiotics listed in Table 7 below were added if necessary. In addition, in Table 7, "Amp" denotes ampicillin, "Km" denotes kanamycin (SIGMA), "Str" denotes streptomycin, and "Tet" denotes tetracycline.

TABLE 7

| Recombinant *E. coli* | Antibiotic (final concentration) |
|---|---|
| A/BL21 | 50 µg/ml Amp |
| B/BL21 | 50 µg/ml Amp, 50 µg/ml Km |
| C/BL21 | 50 µg/ml Amp, 50 µg/ml Str |
| D/BL21 | 50 µg/ml Amp, 30 µg/ml Str |
| E/BL21 | 50 µg/ml Amp, 50 µg/ml Str, 30 µg/ml Km |
| F/BL21 | 50 µg/ml Amp, 50 µg/ml Str, 30 µg/ml Km |
| A/NB | 50 µg/ml Amp, 12.5 µg/ml Tet |
| B/NB | 50 µg/ml Amp, 50 µg/ml Km, 12.5 µg/ml Tet |
| C/NB | 50 µg/ml Amp, 50 µg/ml Str, 12.5 µg/ml Tet |
| D/NB | 50 µg/ml Amp, 30 µg/ml Str, 12.5 µg/ml Tet |
| E/NB | 50 µg/ml Amp, 50 µg/ml Str, 30 µg/ml Km, 12.5 µg/ml Tet |
| F/NB | 50 µg/ml Amp, 50 µg/ml Str, 30 µg/ml Km, 12.5 µg/ml Tet |

A single colony of each of the thus obtained recombinant *Escherichia coli* strains was inoculated in 5 ml of the SD-7 medium containing glucose (Wako Pure Chemical Industries, Ltd.) with a final concentration of 2% and then cultured overnight at 37 degree C. Next, 50 ml of the SD-8 medium containing glucose with a final concentration of 2% was added to a 500-ml buffled Erlenmeyer flask, 500 µl of the culture solution cultured overnight was inoculated, and then culture was performed at 37 degree C. and 130 rpm. When O.D 600 was found to be 1.0 or less, IPTG with a final concentration of 0.1 mM was added, and then culture was further continued. At 0, 3, 6, 9, 24, and 30 hours after addition of IPTG, 5 ml of the culture solution was dispensed into a screw capped test tube and then it was stored at −30 degree C. (this was performed for some solutions even at 48 hours after addition of IPTG). In addition, glucose was additionally added so that the final concentration would be 2% at 24 hours after addition of IPTG.

Subsequently, the culture solution cryopreserved at −30 degree C. was thawed at room temperature. After stirred well with Vortex, 1 ml of the culture solution was added to an Eppendorf tube that had been weighed in advance, and then centrifuged using a mini refrigerated centrifuge (TOMY) at 13000 rpm and 4 degree C. for 10 minutes. Eppendorf tubes from which supernatants had been removed were dried using Speed Vac (SAVANT) with a low temperature for about 4 hours. Subsequently, the weight of each Eppendorf tube was measured, and then the previously measured weight was subtracted therefrom. The thus obtained value was determined to be the dry weight of cells.

Each screw capped test tube containing the remaining culture solution (4 ml) was centrifuged using a bench-top centrifuge LC-230 (TOMY) at 1000 g and room temperature for 5 minutes, thereby separating it into a supernatant and cells.

Two (2) ml of the supernatant was added to a 20-ml head space crimp vial, the vial was capped, and then the vial was placed in hot bath water at 60 degree C. for 15 minutes. Subsequently, component analysis was conducted by GC-MS/HSS for isopropanol and the like.

As GC-MS/HSS, an HP6890/5973/7694 GC-MS/HSS system (Hewlett-Packard) was used. A column used herein was J&DB-624 (0.32 mm×60 m, film thickness: 1.8 μm). Analytical conditions are as follows.
<GC-MS Analytical Conditions>
[Inlet Parameters]
Inlet temperature: 260 degree C.
Split ratio: 1/20
Carrier gas: helium 1.0 ml/minute
[Oven Heating Conditions]
Heat at 40 degree C. for 5 minutes
Heat (5 degree C./minute) to 75 degree C.
Heat (100 degree C./minute) to 260 degree C.
[Detector Conditions]
Detector temperature: 260 degree C.
<Head Space Sampler Conditions>
[Zoom Temp]
Oven: 60 degree C.
Loop: 150 degree C.
Transfer Line: 200 degree C.
[Event Time]
GC Cycle Time: 35 minutes
Vial EQ Time: 15 minutes
Pressuriz. Time: 0.5 minutes
Loop Fill Time: 0.2 minutes
Loop EQ Time: 0.2 minutes
Inject Time: 1.0 minutes
[Vial Parameter]
Shake: HIGH
[Others]
Vial pressurization: 15 psi
<Standard Substances>
Ethanol (specific gravity: 0.789)
Acetone (specific gravity: 0.789)
Isopropanol (specific gravity: 0.784)
Acetic acid (specific gravity: 1.05)

The above standard substances were adjusted to be appropriate concentrations. Concentrations (% (V/V)) were calculated from a calibration curve. Furthermore, the weights and concentrations were calculated while specific gravity was taken into consideration. The amounts of acetone and isopropanol produced by recombinant *Escherichia coli* strains prepared in this reference example are as summarized in Table 8 below.

TABLE 8

| Strain | Time for culture(hr) | Acetone (mg/L) | Time for culture (hr) | Isopropanol (mg/L) |
|---|---|---|---|---|
| BL21 | 6 | 1.8 | — | 0.0 |
| A/BL21 | 9 | 2.7 | — | 0.0 |
| B/BL21 | 24 | 7.6 | 30 | 11.1 |
| C/BL21 | 30 | 1643.7 | 30 | 6.1 |
| D/BL21 | 9 | 209.7 | — | 0.0 |
| E/BL21 | 30 | 586.4 | 30 | 2132.7 |
| F/BL21 | 30 | 136.0 | 30 | 348.4 |
| NB | 24 | 0.6 | — | 0.0 |
| A/NB | 30 | 0.5 | — | 0.0 |
| B/NB | 24 | 0.2 | 30 | 0.7 |
| C/NB | 30 | 1242.2 | 30 | 6.0 |
| D/NB | 9 | 149.0 | — | 0.0 |
| E/NB | 48 | 172.2 | 48 | 1604.3 |
| F/NB | 24 | 5.5 | 24 | 120.9 |

It was understood by the results that the acetone production amount was decreased but the isopropanol production amount was improved in recombinant *Escherichia coli* strains in which the pdh gene had been introduced in addition to the ctfAB gene and the adc gene. It was further understood that the isopropanol production amount was found to be significantly improved in a recombinant *Escherichia coli* strain prepared by introducing the acetoacetyl CoA synthase gene to recombinant *Escherichia coli* in which the ctfAB gene, the adc gene, and the pdh gene had been introduced. However, an effect of improving isopropanaol productivity of acetoacetyl CoA synthase genes, particularly a gene encoding an enzyme that uses malonyl CoA and acetyl CoA as substrates, was lower than that of a gene encoding an enzyme that uses two molecules of acetyl CoA as substrates. On the other hand, in Example 1, the use of the acetoacetyl CoA synthase gene encoding an enzyme that uses malonyl CoA and acetyl CoA as substrates could improve isopropanol productivity even more significantly. Specifically, the result obtained in Example 1 can be said to be a result unpredictable from the findings obtained using recombinant *Escherichia coli* in which the acetoacetyl CoA synthase gene and the isopropanol-biosynthesis-related gene group had been introduced.

Sequence Listing

The invention claimed is:

1. A method for producing isopropanol, comprising culturing recombinant yeast into which a heterologous acetoacetyl CoA synthase gene encoding an enzyme that catalyzes a reaction for conversion of acetyl CoA and malonyl CoA to acetoacetyl CoA and an isopropanol-biosynthesis-related gene group associated with a metabolic pathway for synthesis of isopropanol from acetoacetyl CoA are introduced, wherein the acetoacetyl CoA synthase gene is a gene (ORFn gene) obtained from a microorganism of the genus *Streptomyces* and the isopropanol-biosynthesis-related gene group comprises an isopropanol dehydrogenase gene (pdh gene) from a *Clostridium-beijerinckii*, thereby obtaining a recombinant yeast expressing the ORFn gene and the pdh gene, and then obtaining isopropanol from the culture product of the recombinant yeast.

2. The method for producing isopropanol according to claim 1, wherein the acetoacetyl CoA synthase gene encodes a protein having the amino acid sequence according to SEQ ID NO: 1.

3. The method for producing isopropanol according to claim 1, wherein the acetoacetyl CoA synthase gene and the isopropanol-biosynthesis-related gene group are introduced into the genome of yeast as a host.

* * * * *

UNITED STATES PATENT AND TRADEMARK OFFICE
CERTIFICATE OF CORRECTION

| | |
|---|---|
| PATENT NO. | : 8,828,693 B2 |
| APPLICATION NO. | : 13/697626 |
| DATED | : September 9, 2014 |
| INVENTOR(S) | : Masayoshi Muramatsu and Satoshi Yoneda |

It is certified that error appears in the above-identified patent and that said Letters Patent is hereby corrected as shown below:

On the title page, column 1, item (73) Assignee; should read as follows:

--(73) Assignee: Toyota Jidosha Kabushiki Kaisha, Aichi-ken (JP)--

Signed and Sealed this
Thirty-first Day of March, 2015

Michelle K. Lee
*Director of the United States Patent and Trademark Office*

SEQUENCE LISTING

```
<160> NUMBER OF SEQ ID NOS: 49

<210> SEQ ID NO 1
<211> LENGTH: 329
<212> TYPE: PRT
<213> ORGANISM: Streptomyces sp.

<400> SEQUENCE: 1

Met Thr Asp Val Arg Phe Arg Ile Ile Gly Thr Gly Ala Tyr Val Pro
1               5                   10                  15

Glu Arg Ile Val Ser Asn Asp Glu Val Gly Ala Pro Ala Gly Val Asp
            20                  25                  30

Asp Asp Trp Ile Thr Arg Lys Thr Gly Ile Arg Gln Arg Arg Trp Ala
        35                  40                  45
```

```
Ala Asp Asp Gln Ala Thr Ser Asp Leu Ala Thr Ala Ala Gly Arg Ala
         50                  55                  60

Ala Leu Lys Ala Ala Gly Ile Thr Pro Glu Gln Leu Thr Val Ile Ala
 65                  70                  75                  80

Val Ala Thr Ser Thr Pro Asp Arg Pro Gln Pro Pro Thr Ala Ala Tyr
                 85                  90                  95

Val Gln His His Leu Gly Ala Thr Gly Thr Ala Ala Phe Asp Val Asn
                100                 105                 110

Ala Val Cys Ser Gly Thr Val Phe Ala Leu Ser Ser Val Ala Gly Thr
            115                 120                 125

Leu Val Tyr Arg Gly Gly Tyr Ala Leu Val Ile Gly Ala Asp Leu Tyr
            130                 135                 140

Ser Arg Ile Leu Asn Pro Ala Asp Arg Lys Thr Val Val Leu Phe Gly
145                 150                 155                 160

Asp Gly Ala Gly Ala Met Val Leu Gly Pro Thr Ser Thr Gly Thr Gly
                165                 170                 175

Pro Ile Val Arg Arg Val Ala Leu His Thr Phe Gly Gly Leu Thr Asp
                180                 185                 190

Leu Ile Arg Val Pro Ala Gly Gly Ser Arg Gln Pro Leu Asp Thr Asp
            195                 200                 205

Gly Leu Asp Ala Gly Leu Gln Tyr Phe Ala Met Asp Gly Arg Glu Val
            210                 215                 220

Arg Arg Phe Val Thr Glu His Leu Pro Gln Leu Ile Lys Gly Phe Leu
225                 230                 235                 240

His Glu Ala Gly Val Asp Ala Ala Asp Ile Ser His Phe Val Pro His
                245                 250                 255

Gln Ala Asn Gly Val Met Leu Asp Glu Val Phe Gly Glu Leu His Leu
                260                 265                 270

Pro Arg Ala Thr Met His Arg Thr Val Glu Thr Tyr Gly Asn Thr Gly
            275                 280                 285

Ala Ala Ser Ile Pro Ile Thr Met Asp Ala Ala Val Arg Ala Gly Ser
            290                 295                 300

Phe Arg Pro Gly Glu Leu Val Leu Leu Ala Gly Phe Gly Gly Gly Met
305                 310                 315                 320

Ala Ala Ser Phe Ala Leu Ile Glu Trp
                325

<210> SEQ ID NO 2
<211> LENGTH: 392
<212> TYPE: PRT
<213> ORGANISM: Clostridium acetobutylicum

<400> SEQUENCE: 2

Met Lys Glu Val Val Ile Ala Ser Ala Val Arg Thr Ala Ile Gly Ser
 1               5                  10                  15

Tyr Gly Lys Ser Leu Lys Asp Val Pro Ala Val Asp Leu Gly Ala Thr
                20                  25                  30

Ala Ile Lys Glu Ala Val Lys Lys Ala Gly Ile Lys Pro Glu Asp Val
             35                 40                  45

Asn Glu Val Ile Leu Gly Asn Val Leu Gln Ala Gly Leu Gly Gln Asn
         50                  55                  60

Pro Ala Arg Gln Ala Ser Phe Lys Ala Gly Leu Pro Val Glu Ile Pro
 65                  70                  75                  80

Ala Met Thr Ile Asn Lys Val Cys Gly Ser Gly Leu Arg Thr Val Ser
```

```
                    85                  90                  95
Leu Ala Ala Gln Ile Ile Lys Ala Gly Asp Ala Asp Val Ile Ile Ala
                100                 105                 110

Gly Gly Met Glu Asn Met Ser Arg Ala Pro Tyr Leu Ala Asn Asn Ala
                115                 120                 125

Arg Trp Gly Tyr Arg Met Gly Asn Ala Lys Phe Val Asp Glu Met Ile
130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Ala Ile Lys Ser
                180                 185                 190

Gly Gln Phe Lys Asp Glu Ile Val Pro Val Val Ile Lys Gly Arg Lys
                195                 200                 205

Gly Glu Thr Val Val Asp Thr Asp Glu His Pro Arg Phe Gly Ser Thr
210                 215                 220

Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
                260                 265                 270

Ala Lys Ile Val Ser Tyr Gly Ser Ala Gly Val Asp Pro Ala Ile Met
                275                 280                 285

Gly Tyr Gly Pro Phe Tyr Ala Thr Lys Ala Ala Ile Glu Lys Ala Gly
                290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
                325                 330                 335

Val Asn Val Asn Gly Gly Ala Ile Ala Leu Gly His Pro Ile Gly Ala
                340                 345                 350

Ser Gly Ala Arg Ile Leu Val Thr Leu Val His Ala Met Gln Lys Arg
                355                 360                 365

Asp Ala Lys Lys Gly Leu Ala Thr Leu Cys Ile Gly Gly Gly Gln Gly
                370                 375                 380

Thr Ala Ile Leu Leu Glu Lys Cys
385                 390

<210> SEQ ID NO 3
<211> LENGTH: 218
<212> TYPE: PRT
<213> ORGANISM: Clostridium acetobutylicum

<400> SEQUENCE: 3

Met Asn Ser Lys Ile Ile Arg Phe Glu Asn Leu Arg Ser Phe Phe Lys
1                   5                   10                  15

Asp Gly Met Thr Ile Met Ile Gly Gly Phe Leu Asn Cys Gly Thr Pro
                20                  25                  30

Thr Lys Leu Ile Asp Phe Leu Val Asn Leu Asn Ile Lys Asn Leu Thr
                35                  40                  45

Ile Ile Ser Asn Asp Thr Cys Tyr Pro Asn Thr Gly Ile Gly Lys Leu
50                  55                  60
```

```
Ile Ser Asn Asn Gln Val Lys Lys Leu Ile Ala Ser Tyr Ile Gly Ser
 65                  70                  75                  80

Asn Pro Asp Thr Gly Lys Lys Leu Phe Asn Asn Glu Leu Glu Val Glu
                 85                  90                  95

Leu Ser Pro Gln Gly Thr Leu Val Glu Arg Ile Arg Ala Gly Gly Ser
            100                 105                 110

Gly Leu Gly Gly Val Leu Thr Lys Thr Gly Leu Gly Thr Leu Ile Glu
            115                 120                 125

Lys Gly Lys Lys Lys Ile Ser Ile Asn Gly Thr Glu Tyr Leu Leu Glu
        130                 135                 140

Leu Pro Leu Thr Ala Asp Val Ala Leu Ile Lys Gly Ser Ile Val Asp
145                 150                 155                 160

Glu Ala Gly Asn Thr Phe Tyr Lys Gly Thr Thr Lys Asn Phe Asn Pro
                165                 170                 175

Tyr Met Ala Met Ala Ala Lys Thr Val Ile Val Glu Ala Glu Asn Leu
                180                 185                 190

Val Ser Cys Glu Lys Leu Glu Lys Glu Lys Ala Met Thr Pro Gly Val
            195                 200                 205

Leu Ile Asn Tyr Ile Val Lys Glu Pro Ala
        210                 215

<210> SEQ ID NO 4
<211> LENGTH: 221
<212> TYPE: PRT
<213> ORGANISM: Clostridium acetobutylicum

<400> SEQUENCE: 4

Met Ile Asn Asp Lys Asn Leu Ala Lys Glu Ile Ile Ala Lys Arg Val
  1               5                  10                  15

Ala Arg Glu Leu Lys Asn Gly Gln Leu Val Asn Leu Gly Val Gly Leu
                 20                  25                  30

Pro Thr Met Val Ala Asp Tyr Ile Pro Lys Asn Phe Lys Ile Thr Phe
             35                  40                  45

Gln Ser Glu Asn Gly Ile Val Gly Met Gly Ala Ser Pro Lys Ile Asn
 50                  55                  60

Glu Ala Asp Lys Asp Val Val Asn Ala Gly Gly Asp Tyr Thr Thr Val
 65                  70                  75                  80

Leu Pro Asp Gly Thr Phe Phe Asp Ser Ser Val Ser Phe Ser Leu Ile
                 85                  90                  95

Arg Gly Gly His Val Asp Val Thr Val Leu Gly Ala Leu Gln Val Asp
            100                 105                 110

Glu Lys Gly Asn Ile Ala Asn Trp Ile Val Pro Gly Lys Met Leu Ser
        115                 120                 125

Gly Met Gly Gly Ala Met Asp Leu Val Asn Gly Ala Lys Lys Val Ile
    130                 135                 140

Ile Ala Met Arg His Thr Asn Lys Gly Gln Pro Lys Ile Leu Lys Lys
145                 150                 155                 160

Cys Thr Leu Pro Leu Thr Ala Lys Ser Gln Ala Asn Leu Ile Val Thr
                165                 170                 175

Glu Leu Gly Val Ile Glu Val Ile Asn Asp Gly Leu Leu Leu Thr Glu
            180                 185                 190

Ile Asn Lys Asn Thr Thr Ile Asp Glu Ile Arg Ser Leu Thr Ala Ala
        195                 200                 205

Asp Leu Leu Ile Ser Asn Glu Leu Arg Pro Met Ala Val
    210                 215                 220
```

<210> SEQ ID NO 5
<211> LENGTH: 244
<212> TYPE: PRT
<213> ORGANISM: Clostridium acetobutylicum

<400> SEQUENCE: 5

Met Leu Lys Asp Glu Val Ile Lys Gln Ile Ser Thr Pro Leu Thr Ser
1               5                   10                  15

Pro Ala Phe Pro Arg Gly Pro Tyr Lys Phe His Asn Arg Glu Tyr Phe
            20                  25                  30

Asn Ile Val Tyr Arg Thr Asp Met Asp Ala Leu Arg Lys Val Val Pro
        35                  40                  45

Glu Pro Leu Glu Ile Asp Glu Pro Leu Val Arg Phe Glu Ile Met Ala
    50                  55                  60

Met His Asp Thr Ser Gly Leu Gly Cys Tyr Thr Glu Ser Gly Gln Ala
65                  70                  75                  80

Ile Pro Val Ser Phe Asn Gly Val Lys Gly Asp Tyr Leu His Met Met
                85                  90                  95

Tyr Leu Asp Asn Glu Pro Ala Ile Ala Val Gly Arg Glu Leu Ser Ala
            100                 105                 110

Tyr Pro Lys Lys Leu Gly Tyr Pro Lys Leu Phe Val Asp Ser Asp Thr
        115                 120                 125

Leu Val Gly Thr Leu Asp Tyr Gly Lys Leu Arg Val Ala Thr Ala Thr
    130                 135                 140

Met Gly Tyr Lys His Lys Ala Leu Asp Ala Asn Glu Ala Lys Asp Gln
145                 150                 155                 160

Ile Cys Arg Pro Asn Tyr Met Leu Lys Ile Ile Pro Asn Tyr Asp Gly
                165                 170                 175

Ser Pro Arg Ile Cys Glu Leu Ile Asn Ala Lys Ile Thr Asp Val Thr
            180                 185                 190

Val His Glu Ala Trp Thr Gly Pro Thr Arg Leu Gln Leu Phe Asp His
        195                 200                 205

Ala Met Ala Pro Leu Asn Asp Leu Pro Val Lys Glu Ile Val Ser Ser
    210                 215                 220

Ser His Ile Leu Ala Asp Ile Ile Leu Pro Arg Ala Glu Val Ile Tyr
225                 230                 235                 240

Asp Tyr Leu Lys

<210> SEQ ID NO 6
<211> LENGTH: 351
<212> TYPE: PRT
<213> ORGANISM: Clostridium beijerinckii

<400> SEQUENCE: 6

Met Lys Gly Phe Ala Met Leu Gly Ile Asn Lys Leu Gly Trp Ile Glu
1               5                   10                  15

Lys Glu Arg Pro Val Ala Gly Ser Tyr Asp Ala Ile Val Arg Pro Leu
            20                  25                  30

Ala Val Ser Pro Cys Thr Ser Asp Ile His Thr Val Phe Glu Gly Ala
        35                  40                  45

Leu Gly Asp Arg Lys Asn Met Ile Leu Gly His Glu Ala Val Gly Glu
    50                  55                  60

Val Val Glu Val Gly Ser Glu Val Lys Asp Phe Lys Pro Gly Asp Arg
65                  70                  75                  80

Val Ile Val Pro Cys Thr Thr Pro Asp Trp Arg Ser Leu Glu Val Gln
                85                  90                  95

Ala Gly Phe Gln Gln His Ser Asn Gly Met Leu Ala Gly Trp Lys Phe
            100                 105                 110

Ser Asn Phe Lys Asp Gly Val Phe Gly Glu Tyr Phe His Val Asn Asp
        115                 120                 125

Ala Asp Met Asn Leu Ala Ile Leu Pro Lys Asp Met Pro Leu Glu Asn
    130                 135                 140

Ala Val Met Ile Thr Asp Met Met Thr Thr Gly Phe His Gly Ala Glu
145                 150                 155                 160

Leu Ala Asp Ile Gln Met Gly Ser Ser Val Val Ile Gly Ile Gly
                165                 170                 175

Ala Val Gly Leu Met Gly Ile Ala Gly Ala Lys Leu Arg Gly Ala Gly
            180                 185                 190

Arg Ile Ile Gly Val Gly Ser Arg Pro Ile Cys Val Glu Ala Ala Lys
        195                 200                 205

Phe Tyr Gly Ala Thr Asp Ile Leu Asn Tyr Lys Asn Gly His Ile Val
    210                 215                 220

Asp Gln Val Met Lys Leu Thr Asn Gly Lys Gly Val Asp Arg Val Ile
225                 230                 235                 240

Met Ala Gly Gly Gly Ser Glu Thr Leu Ser Gln Ala Val Ser Met Val
                245                 250                 255

Lys Pro Gly Gly Ile Ile Ser Asn Ile Asn Tyr His Gly Ser Gly Asp
            260                 265                 270

Ala Leu Leu Ile Pro Arg Val Glu Trp Gly Cys Gly Met Ala His Lys
        275                 280                 285

Thr Ile Lys Gly Gly Leu Cys Pro Gly Gly Arg Leu Arg Ala Glu Met
    290                 295                 300

Leu Arg Asp Met Val Val Tyr Asn Arg Val Asp Leu Ser Lys Leu Val
305                 310                 315                 320

Thr His Val Tyr His Gly Phe Asp His Ile Glu Glu Ala Leu Leu Leu
                325                 330                 335

Met Lys Asp Lys Pro Lys Asp Leu Ile Lys Ala Val Val Ile Leu
            340                 345                 350

<210> SEQ ID NO 7
<211> LENGTH: 32
<212> TYPE: DNA
<213> ORGANISM: Artificial
<220> FEATURE:
<223> OTHER INFORMATION: synthetic DNA

<400> SEQUENCE: 7
tagggagctc caagaattac tcgtgagtaa gg                           32

<210> SEQ ID NO 8
<211> LENGTH: 36
<212> TYPE: DNA
<213> ORGANISM: Artificial
<220> FEATURE:
<223> OTHER INFORMATION: synthetic DNA

<400> SEQUENCE: 8
ataaccgcgg tgttttatat ttgttgtaaa aagtag                       36

<210> SEQ ID NO 9
<211> LENGTH: 37
<212> TYPE: DNA

```
<213> ORGANISM: Artificial
<220> FEATURE:
<223> OTHER INFORMATION: synthetic DNA

<400> SEQUENCE: 9
ttaagtcgac attgaattga attgaaatcg atagatc                              37

<210> SEQ ID NO 10
<211> LENGTH: 30
<212> TYPE: DNA
<213> ORGANISM: Artificial
<220> FEATURE:
<223> OTHER INFORMATION: synthetic DNA

<400> SEQUENCE: 10
ttaaggtacc gcttcaagct tacacaacac                                      30

<210> SEQ ID NO 11
<211> LENGTH: 33
<212> TYPE: DNA
<213> ORGANISM: Artificial
<220> FEATURE:
<223> OTHER INFORMATION: synthetic DNA

<400> SEQUENCE: 11
cacggaattc cagttcgagt ttatcattat caa                                  33

<210> SEQ ID NO 12
<211> LENGTH: 35
<212> TYPE: DNA
<213> ORGANISM: Artificial
<220> FEATURE:
<223> OTHER INFORMATION: synthetic DNA

<400> SEQUENCE: 12
ctctggatcc tttgtttgtt tatgtgtgtt tattc                                35

<210> SEQ ID NO 13
<211> LENGTH: 32
<212> TYPE: DNA
<213> ORGANISM: Artificial
<220> FEATURE:
<223> OTHER INFORMATION: synthetic DNA

<400> SEQUENCE: 13
taggcaattg caagaattac tcgtgagtaa gg                                   32

<210> SEQ ID NO 14
<211> LENGTH: 36
<212> TYPE: DNA
<213> ORGANISM: Artificial
<220> FEATURE:
<223> OTHER INFORMATION: synthetic DNA

<400> SEQUENCE: 14
ataagaattc tgttttatat ttgttgtaaa aagtag                               36

<210> SEQ ID NO 15
<211> LENGTH: 1008
<212> TYPE: DNA
<213> ORGANISM: Artificial
<220> FEATURE:
<223> OTHER INFORMATION: synthetic DNA

<400> SEQUENCE: 15
ggatccgcca ccatgacaga tgtcagattc cgtatcattg ggaccggagc ttatgttcct     60
```

-continued

```
gagagaattg tgtccaatga cgaagtgggt gcacctgccg gtgtcgatga cgactggatt    120
accagaaaga ccggtataag gcaacgtaga tgggccgcag acgatcaagc cacttcggat    180
cttgctactg cagctgggag agcagcccta aaagctgccg gcataacacc cgaacagtta    240
acagtaattg ccgttgcgac tagtacccca gacaggccac aacctcctac tgctgcgtat    300
gtacagcatc atcttggcgc tacaggtaca gccgcttttg acgtgaatgc tgtatgttct    360
gggacagtct tcgccttgtc ctctgttgct gggacgttgg tttatagagg aggatacgca    420
ttagtgattg gtgctgactt atacagcagg atactaaacc cagcagatag gaaaactgtg    480
gttctgtttg gtgatggtgc tggtgctatg gttctaggac caacttctac tggaactggt    540
cctatcgttc gtagagtagc cttgcacact tcggtggct aacggactt gattagagta    600 ccagcaggag gctcaagaca accgttggat acagatggtc ttgatgctgg tttgcaatac    660
tttgccatgg atgaagaga ggttagaaga ttcgtcaccg agcatctacc ccagttgatc    720
aagggctttc tgcatgaagc tggggttgat gcggcagata tatcacactt cgttccacat    780
caagcaaacg gtgtgatgtt agatgaagtc tttggcgaat tgcacttacc cagagcaaca    840
atgcatagga cggtagaaac ctatggcaat actggtgctg cgtcaattcc gattacgatg    900
gatgctgcag ttagagctgg ctcttttaga ccaggtgaac tggtcttgtt agcgggtttt    960
ggaggtggta tggcagctag ttttgcactt atcgaatggt aactcgag              1008
```

<210> SEQ ID NO 16
<211> LENGTH: 12
<212> TYPE: DNA
<213> ORGANISM: Artificial
<220> FEATURE:
<223> OTHER INFORMATION: synthetic DNA

<400> SEQUENCE: 16

```
ggatccgcca cc                                                         12
```

<210> SEQ ID NO 17
<211> LENGTH: 42
<212> TYPE: DNA
<213> ORGANISM: Artificial
<220> FEATURE:
<223> OTHER INFORMATION: synthetic DNA

<400> SEQUENCE: 17

```
gggggatcc gccaccatgt ctcagaacgt ttacattgta tc                         42
```

<210> SEQ ID NO 18
<211> LENGTH: 36
<212> TYPE: DNA
<213> ORGANISM: Artificial
<220> FEATURE:
<223> OTHER INFORMATION: synthetic DNA

<400> SEQUENCE: 18

```
ggggctcgag tcatatcttt tcaatgacaa tagagg                               36
```

<210> SEQ ID NO 19
<211> LENGTH: 32
<212> TYPE: DNA
<213> ORGANISM: Artificial
<220> FEATURE:
<223> OTHER INFORMATION: synthetic DNA

<400> SEQUENCE: 19

```
atgttaaagg atgaagtaat taaacaaatt ag                                    32

<210> SEQ ID NO 20
<211> LENGTH: 32
<212> TYPE: DNA
<213> ORGANISM: Artificial
<220> FEATURE:
<223> OTHER INFORMATION: synthetic DNA

<400> SEQUENCE: 20
ttacttaaga taatcatata taacttcagc tc                                    32

<210> SEQ ID NO 21
<211> LENGTH: 50
<212> TYPE: DNA
<213> ORGANISM: Artificial
<220> FEATURE:
<223> OTHER INFORMATION: synthetic DNA

<400> SEQUENCE: 21
ggggacaagt ttgtacaaaa aagcaggctc agttcgagtt tatcattatc                 50

<210> SEQ ID NO 22
<211> LENGTH: 50
<212> TYPE: DNA
<213> ORGANISM: Artificial
<220> FEATURE:
<223> OTHER INFORMATION: synthetic DNA

<400> SEQUENCE: 22
ggggacaact ttgtatagaa aagttgggtg ggccgcaaat taaagccttc                 50

<210> SEQ ID NO 23
<211> LENGTH: 36
<212> TYPE: DNA
<213> ORGANISM: Artificial
<220> FEATURE:
<223> OTHER INFORMATION: synthetic DNA

<400> SEQUENCE: 23
atgaactcta aaataattag atttgaaaat ttaagg                                36

<210> SEQ ID NO 24
<211> LENGTH: 29
<212> TYPE: DNA
<213> ORGANISM: Artificial
<220> FEATURE:
<223> OTHER INFORMATION: synthetic DNA

<400> SEQUENCE: 24
ttatgcaggc tcctttacta tataattta                                        29

<210> SEQ ID NO 25
<211> LENGTH: 48
<212> TYPE: DNA
<213> ORGANISM: Artificial
<220> FEATURE:
<223> OTHER INFORMATION: synthetic DNA

<400> SEQUENCE: 25
ggggacaact tttctataca aagttggctt caagcttaca caacacgg                   48

<210> SEQ ID NO 26
<211> LENGTH: 49
<212> TYPE: DNA
<213> ORGANISM: Artificial
```

```
<220> FEATURE:
<223> OTHER INFORMATION: synthetic DNA

<400> SEQUENCE: 26
ggggacaact ttattataca aagttgtcaa gaattactcg tgagtaagg            49

<210> SEQ ID NO 27
<211> LENGTH: 28
<212> TYPE: DNA
<213> ORGANISM: Artificial
<220> FEATURE:
<223> OTHER INFORMATION: synthetic DNA

<400> SEQUENCE: 27
atgattaatg ataaaaacct agcgaaag                                   28

<210> SEQ ID NO 28
<211> LENGTH: 24
<212> TYPE: DNA
<213> ORGANISM: Artificial
<220> FEATURE:
<223> OTHER INFORMATION: synthetic DNA

<400> SEQUENCE: 28
ctaaacagcc atgggtctaa gttc                                       24

<210> SEQ ID NO 29
<211> LENGTH: 30
<212> TYPE: DNA
<213> ORGANISM: Artificial
<220> FEATURE:
<223> OTHER INFORMATION: synthetic DNA

<400> SEQUENCE: 29
tagtggatcc gatgattaat gataaaaacc                                 30

<210> SEQ ID NO 30
<211> LENGTH: 22
<212> TYPE: DNA
<213> ORGANISM: Artificial
<220> FEATURE:
<223> OTHER INFORMATION: synthetic DNA

<400> SEQUENCE: 30
cctagacttc aggttgtcta ac                                         22

<210> SEQ ID NO 31
<211> LENGTH: 46
<212> TYPE: DNA
<213> ORGANISM: Artificial
<220> FEATURE:
<223> OTHER INFORMATION: synthetic DNA

<400> SEQUENCE: 31
ggggacaact ttgtataata aagttgggcc gcaaattaaa gccttc                46

<210> SEQ ID NO 32
<211> LENGTH: 51
<212> TYPE: DNA
```

<213> ORGANISM: Artificial
<220> FEATURE:
<223> OTHER INFORMATION: synthetic DNA

<400> SEQUENCE: 32
ggggaccact tgtacaaga aagctgggta cagttcgagt ttatcattat c        51

<210> SEQ ID NO 33
<211> LENGTH: 35
<212> TYPE: DNA
<213> ORGANISM: Artificial
<220> FEATURE:
<223> OTHER INFORMATION: synthetic DNA

<400> SEQUENCE: 33
tagggagctc atcacaagtt tgtacaaaaa agctg                         35

<210> SEQ ID NO 34
<211> LENGTH: 33
<212> TYPE: DNA
<213> ORGANISM: Artificial
<220> FEATURE:
<223> OTHER INFORMATION: synthetic DNA

<400> SEQUENCE: 34
ttaaggtacc atcaccactt tgtacaagaa agc                           33

<210> SEQ ID NO 35
<211> LENGTH: 1097
<212> TYPE: DNA
<213> ORGANISM: Artificial
<220> FEATURE:
<223> OTHER INFORMATION: synthetic DNA

<400> SEQUENCE: 35
cgggtttccg cggtctagag ccaccatgaa aggtttcgca atgttgggta tcaataagtt    60
aggctggata gagaaagaaa gacctgtcgc aggtagctat gatgccattg ttcgaccatt   120
agccgttcct ccttgcacat ccgacattca cacagtgttt gaaggtgcat taggagatag   180
gaagaacatg atactgggtc atgaagccgt cggagaagta gttgaagttg gaagcgaagt   240
aaaggacttt aagcctggtg atagagtgat cgttccttgc acaactccag attggagatc   300
attagaagtt caagctggat ccaacagca ttctaatggc atgcttgctg gttggaaatt   360
cagtaatttc aaggatggcg tgtttggtga gtactttcat gtcaatgatg cagatatgaa   420
cctagctatt cttcccaagg atatgccatt ggagaatgct gtcatgataa ccgacatgat   480
gactactggg tttcatggtg ctgaactagc ggacattcag atgggttcat cggttgttgt   540
gattggtatt ggtgctgttg gacttatggg gattgcaggc gcaaaattgc gtggtgccgg   600
ccgtatcatt ggcgtaggtt cgagacccat atgtgtggaa gctgcgaaat ctatggtgc    660
tacagacatt ttgaactaca gaatggtca catagttgac caagtcatga aactgaccaa   720
tgggaaaggc gttgataggg tgattatggc tggtggtgga tctgaaactt tgagtcaagc   780
cgtctctatg gtaaaaccag gtggaatcat atccaatatc aactaccatg ggtcaggaga   840
tgcgttactt ataccgagag ttgagtgggg atgtggcatg gcacacaaaa cgattaaggg   900
tggtttatgt ccaggcggaa gattaagagc tgaaatgtta agagatatgg ttgtatataa   960
caggggttgat ctgtccaaac tagtgacgca tgtatatcac gggtttgatc atatcgagga  1020
agcattgttg ttgatgaaag ataaaccgaa agacctaatc aaggccgtag tcattttgta  1080
aggatccgtc gacgggg                                               1097

<210> SEQ ID NO 36
<211> LENGTH: 25
<212> TYPE: DNA
<213> ORGANISM: Artificial
<220> FEATURE:
<223> OTHER INFORMATION: synthetic DNA

<400> SEQUENCE: 36
ggggtttccg cggtctagag ccacc                                          25

<210> SEQ ID NO 37
<211> LENGTH: 16
<212> TYPE: DNA
<213> ORGANISM: Artificial
<220> FEATURE:
<223> OTHER INFORMATION: synthetic DNA

<400> SEQUENCE: 37
ggatccgtcg acgggg                                                    16

<210> SEQ ID NO 38
<211> LENGTH: 28
<212> TYPE: DNA
<213> ORGANISM: Artificial
<220> FEATURE:
<223> OTHER INFORMATION: synthetic DNA

<400> SEQUENCE: 38
atgaaagaag ttgtaatagc tagtgcag                                       28

<210> SEQ ID NO 39
<211> LENGTH: 26
<212> TYPE: DNA
<213> ORGANISM: Artificial
<220> FEATURE:
<223> OTHER INFORMATION: synthetic DNA

<400> SEQUENCE: 39
ctagcacttt tctagcaata ttgctg                                         26

<210> SEQ ID NO 40
<211> LENGTH: 26
<212> TYPE: DNA
<213> ORGANISM: Artificial
<220> FEATURE:
<223> OTHER INFORMATION: synthetic DNA

<400> SEQUENCE: 40
aaacatatga agaagttgt aatagc                                          26

<210> SEQ ID NO 41
<211> LENGTH: 28
<212> TYPE: DNA
<213> ORGANISM: Artificial
<220> FEATURE:
<223> OTHER INFORMATION: synthetic DNA

<400> SEQUENCE: 41
aaactcgagc tagcactttt ctagcaat                                       28

<210> SEQ ID NO 42
<211> LENGTH: 29
<212> TYPE: DNA
<213> ORGANISM: Artificial
<220> FEATURE:

<223> OTHER INFORMATION: synthetic DNA

<400> SEQUENCE: 42
aaacatatga ccgacgtccg attccgcat                                    29

<210> SEQ ID NO 43
<211> LENGTH: 29
<212> TYPE: DNA
<213> ORGANISM: Artificial
<220> FEATURE:
<223> OTHER INFORMATION: synthetic DNA

<400> SEQUENCE: 43
aaactcgagt taccactcga tcagggcga                                    29

<210> SEQ ID NO 44
<211> LENGTH: 44
<212> TYPE: DNA
<213> ORGANISM: Artificial
<220> FEATURE:
<223> OTHER INFORMATION: synthetic DNA

<400> SEQUENCE: 44
attcatatga actctaaaat aattagattt gaaaatttaa ggtc                   44

<210> SEQ ID NO 45
<211> LENGTH: 30
<212> TYPE: DNA
<213> ORGANISM: Artificial
<220> FEATURE:
<223> OTHER INFORMATION: synthetic DNA

<400> SEQUENCE: 45
agactcgagc taaacagcca tgggtctaag                                   30

<210> SEQ ID NO 46
<211> LENGTH: 46
<212> TYPE: DNA
<213> ORGANISM: Artificial
<220> FEATURE:
<223> OTHER INFORMATION: synthetic DNA

<400> SEQUENCE: 46
cacgtcgaca aggagatata atgttaaagg atgaagtaat taaaca                 46

<210> SEQ ID NO 47
<211> LENGTH: 41
<212> TYPE: DNA
<213> ORGANISM: Artificial
<220> FEATURE:
<223> OTHER INFORMATION: synthetic DNA

<400> SEQUENCE: 47
cacgcggccg cttacttaag ataatcatat ataacttcag c                      41

<210> SEQ ID NO 48
<211> LENGTH: 28
<212> TYPE: DNA
<213> ORGANISM: Artificial
<220> FEATURE:
<223> OTHER INFORMATION: synthetic DNA

<400> SEQUENCE: 48
ggaattccat gaaaggtttc gcaatgtt                                     28

```
<210> SEQ ID NO 49
<211> LENGTH: 39
<212> TYPE: DNA
<213> ORGANISM: Artificial
<220> FEATURE:
<223> OTHER INFORMATION: synthetic DNA

<400> SEQUENCE: 49
aactgcagaa ccaatgcatt ggttacaaaa tgactacgg                    39
```